US011299764B2

(12) United States Patent
Hunsley et al.

(10) Patent No.: US 11,299,764 B2
(45) Date of Patent: *Apr. 12, 2022

(54) SINGLE SPIN PROCESS FOR BLOOD PLASMA SEPARATION AND PLASMA COMPOSITION INCLUDING PRESERVATIVE

(71) Applicant: STRECK, INC., La Vista, NE (US)

(72) Inventors: Bradford A. Hunsley, Papillion, NE (US); Jianbing Qin, Omaha, NE (US)

(73) Assignee: STRECK, INC., La Vista, NE (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/233,880

(22) Filed: Dec. 27, 2018

(65) Prior Publication Data

US 2019/0127780 A1 May 2, 2019

Related U.S. Application Data

(63) Continuation of application No. 15/355,444, filed on Nov. 18, 2016, now abandoned.

(60) Provisional application No. 62/258,404, filed on Nov. 20, 2015.

(51) Int. Cl.
*C12Q 1/68* (2018.01)
*C12N 15/10* (2006.01)
*C12Q 1/6806* (2018.01)
*C12Q 1/686* (2018.01)

(52) U.S. Cl.
CPC ....... *C12Q 1/6806* (2013.01); *C12N 15/1003* (2013.01); *C12Q 1/686* (2013.01)

(58) Field of Classification Search
CPC .................. C12Q 2523/32; C12N 15/1003
See application file for complete search history.

(56) References Cited

U.S. PATENT DOCUMENTS

| | | |
|---|---|---|
| 1,432,249 A | 10/1922 | Robert |
| 1,922,799 A | 8/1933 | Gaus |
| 2,250,666 A | 7/1941 | Webb |
| 2,690,624 A | 10/1954 | Phillips |
| 2,930,570 A | 3/1960 | Leedy |
| 3,781,120 A | 12/1973 | Engelhardt |
| 3,867,521 A | 2/1975 | Miskel et al. |
| 3,872,730 A | 3/1975 | Ringrose et al. |
| 3,874,384 A | 4/1975 | Deindoerfer et al. |
| 3,879,295 A | 4/1975 | Glover et al. |
| 3,973,913 A | 8/1976 | Louderback |
| 3,994,085 A | 11/1976 | Groselak et al. |
| 4,043,453 A | 8/1977 | Greenlee |
| 4,318,090 A | 3/1982 | Narlow et al. |
| 4,436,821 A | 3/1984 | Ryan |
| 4,513,522 A | 4/1985 | Selenke |
| 4,515,890 A | 5/1985 | Manderino et al. |
| 4,579,759 A | 4/1986 | Breuers |
| 4,584,219 A | 4/1986 | Baartmans |
| 4,675,159 A | 6/1987 | Al-Sioufi |
| 4,818,700 A | 4/1989 | Cregg et al. |
| 4,884,827 A | 12/1989 | Kelley |
| 4,921,277 A | 5/1990 | McDonough |
| 5,000,484 A | 3/1991 | Phelan et al. |
| 5,060,672 A | 10/1991 | Irimi et al. |
| 5,110,908 A | 5/1992 | Deich et al. |
| 5,135,125 A | 8/1992 | Andel et al. |
| 5,196,182 A | 3/1993 | Ryan |
| 5,213,765 A | 5/1993 | Kasai et al. |
| 5,250,438 A | 10/1993 | Ryan |
| 5,257,633 A | 11/1993 | Vogler et al. |
| 5,260,048 A | 11/1993 | Ryan |
| 5,270,208 A | 12/1993 | Ryan |
| 5,343,647 A | 9/1994 | Bulka |
| 5,366,249 A | 11/1994 | Diemert |
| 5,429,797 A | 7/1995 | Camiener |
| 5,447,842 A | 9/1995 | Simons |
| 5,457,024 A | 10/1995 | Goldbard |
| 5,459,073 A | 10/1995 | Ryan |
| 5,459,253 A | 10/1995 | Wolin et al. |
| 5,460,797 A | 10/1995 | Ryan |

(Continued)

FOREIGN PATENT DOCUMENTS

| | | |
|---|---|---|
| AU | 2008288601 A1 | 4/2009 |
| CA | 2406463 A1 | 11/2001 |

(Continued)

OTHER PUBLICATIONS

Finning K, Martin P, Daniels G. The use of maternal plasma for prenatal RhD blood group genotyping. Methods Mol Biol. 2009; 496: 143-57. (Year: 2009).*
Anitua E. Plasma rich in growth factors: preliminary results of use in the preparation of future sites for implants. Int J Oral Maxillofac Implants. Jul.-Aug. 1999; 14(4):529-35. (Year: 1999).*
Ammerlaan W, Trezzi JP, Lescuyer P, Mathay C, Hiller K, Betsou F. Method validation for preparing serum and plasma samples from human blood for downstream proteomic, metabolomic, and circulating nucleic acid-based applications. Biopreserv Biobank. Aug. 2014; 12(4):269-80. Epub Jul. 30, 2014. (Year: 2014).*
Banfi G, Salvagno GL, Lippi G. The role of ethylenediamine tetraacetic acid (EDTA) as in vitro anticoagulant for diagnostic purposes. Clin Chem Lab Med. 2007; 45(5):565-76. (Year: 2007).*
Hindson et al. High-throughput droplet digital PCR system for absolute quantitation of DNA copy number. Anal Chem. Nov. 15, 2011; 83(22):8604-10. Epub Oct. 28, 2011. (Year: 2011).*

(Continued)

*Primary Examiner* — Christopher M Babic
*Assistant Examiner* — Olayinka A Oyeyemi
(74) *Attorney, Agent, or Firm* — Marshall, Gerstein & Borun LLP

(57) ABSTRACT

A screening method for the identification of a characteristic of a target nucleic acid in a whole blood sample, including positioning a composition comprising whole blood and at least one preservative agent within a centrifuge, centrifugating the composition to isolate a plasma that includes at least one target nucleic acid for further analysis and analyzing the at least one target nucleic acid to identify a characteristic about the at least one target nucleic acid, and a composition including the plasma, the preservative agent, and any other ingredient, which is produced by the method.

48 Claims, 3 Drawing Sheets

(56) References Cited

U.S. PATENT DOCUMENTS

| | | |
|---|---|---|
| 5,468,022 A | 11/1995 | Linder et al. |
| 5,490,658 A | 2/1996 | Coward et al. |
| 5,501,954 A | 3/1996 | Mahr et al. |
| 5,501,963 A | 3/1996 | Burckhardt |
| 5,512,343 A | 4/1996 | Shaw |
| 5,538,871 A | 7/1996 | Nuovo et al. |
| 5,540,358 A | 7/1996 | Wiles et al. |
| 5,560,657 A | 10/1996 | Morgan |
| 5,614,391 A | 3/1997 | Franciskovich et al. |
| 5,618,664 A | 4/1997 | Kiessling |
| 5,629,147 A | 5/1997 | Asgari et al. |
| D382,343 S | 8/1997 | Wandell et al. |
| 5,654,054 A | 8/1997 | Tropsha et al. |
| 5,688,516 A | 11/1997 | Raad et al. |
| 5,731,156 A | 3/1998 | Golbus |
| 5,741,638 A | 4/1998 | Yamane |
| 5,783,093 A | 7/1998 | Holme |
| 5,811,099 A | 9/1998 | Ryan |
| 5,817,519 A | 10/1998 | Zelmanovic et al. |
| 5,849,517 A | 12/1998 | Ryan |
| 5,858,699 A | 1/1999 | Granger et al. |
| 5,861,253 A | 1/1999 | Asgari et al. |
| 5,888,822 A | 3/1999 | Hengstenberg |
| 5,906,744 A | 5/1999 | Carroll et al. |
| 5,939,259 A | 8/1999 | Harvey et al. |
| 5,962,234 A | 10/1999 | Golbus |
| 5,976,014 A | 11/1999 | Petrick et al. |
| 5,977,153 A | 11/1999 | Camiener |
| 5,985,572 A | 11/1999 | MacFarlane |
| 6,013,240 A | 1/2000 | Behr et al. |
| 6,030,767 A | 2/2000 | Wagner et al. |
| 6,043,032 A | 3/2000 | Yamagishi |
| 6,072,086 A | 6/2000 | James et al. |
| 6,074,825 A | 6/2000 | Rundell et al. |
| 6,074,827 A | 6/2000 | Nelson et al. |
| 6,077,235 A | 6/2000 | Serpentino et al. |
| 6,125,563 A | 10/2000 | Girerd |
| 6,128,840 A | 10/2000 | Boisvert |
| 6,168,922 B1 | 1/2001 | Harvey et al. |
| 6,177,163 B1 | 1/2001 | Blok et al. |
| 6,190,609 B1 | 2/2001 | Chapman et al. |
| 6,197,539 B1 | 3/2001 | Granger et al. |
| 6,197,540 B1 | 3/2001 | Granger et al. |
| 6,200,500 B1 | 3/2001 | Ryan |
| 6,210,889 B1 | 4/2001 | Drouin et al. |
| 6,218,531 B1 | 4/2001 | Ekenberg |
| 6,221,668 B1 | 4/2001 | Ryan et al. |
| 6,251,638 B1 | 6/2001 | Umansky et al. |
| 6,258,540 B1 | 7/2001 | Lo et al. |
| 6,287,820 B1 | 9/2001 | Umansky et al. |
| 6,337,189 B1 | 1/2002 | Ryan |
| 6,365,362 B1 | 4/2002 | Terstappen et al. |
| 6,399,388 B1 | 6/2002 | Ryan et al. |
| 6,403,377 B1 | 6/2002 | Ryan et al. |
| 6,406,915 B2 | 6/2002 | Ryan et al. |
| 6,527,242 B1 | 3/2003 | Kennedy |
| 6,527,957 B1 | 3/2003 | Deniega et al. |
| 6,551,267 B1 | 4/2003 | Cohen et al. |
| 6,560,847 B2 | 5/2003 | Ohlsson |
| 6,579,672 B1 | 6/2003 | Granger et al. |
| 6,581,973 B2 | 6/2003 | Levine et al. |
| 6,602,718 B1 | 8/2003 | Augello et al. |
| 6,617,170 B2 | 9/2003 | Augello et al. |
| 6,617,180 B1 | 9/2003 | Wang |
| 6,623,983 B1 | 9/2003 | Terstappen et al. |
| 6,630,301 B1 | 10/2003 | Gocke et al. |
| 6,645,731 B2 | 11/2003 | Terstappen et al. |
| 6,664,056 B2 | 12/2003 | Lo et al. |
| 6,759,217 B2 | 7/2004 | Kopreski |
| 6,821,789 B2 | 11/2004 | Augello et al. |
| 6,860,513 B2 | 3/2005 | Kaufman |
| 6,884,573 B2 | 4/2005 | Fischer et al. |
| 6,913,932 B2 | 7/2005 | Maples et al. |
| 6,916,634 B2 | 7/2005 | Kopreski |
| 6,939,671 B2 | 9/2005 | Kopreski |
| 6,994,790 B2 | 2/2006 | Corbin et al. |
| 7,022,478 B2 | 4/2006 | Rainer et al. |
| 7,044,941 B2 | 5/2006 | Mathias et al. |
| 7,208,275 B2 | 4/2007 | Gocke et al. |
| 7,267,980 B1 | 9/2007 | Mortari et al. |
| 7,282,371 B2 | 10/2007 | Helftenbein |
| 7,288,380 B1 | 10/2007 | Gocke et al. |
| 7,318,293 B2 | 1/2008 | Ardern, II |
| 7,332,277 B2 | 2/2008 | Dhallan |
| 7,332,288 B2 | 2/2008 | Terstappen et al. |
| 7,358,039 B2 | 4/2008 | Fischer et al. |
| 7,390,663 B2 | 6/2008 | Ryan et al. |
| 7,398,999 B2 | 7/2008 | Kaufman |
| 7,419,832 B2 | 9/2008 | Hunsley et al. |
| 7,442,506 B2 | 10/2008 | Dhallan |
| 7,445,901 B2 | 11/2008 | Kudlicki et al. |
| 7,478,513 B2 | 1/2009 | Baldwin |
| 7,569,350 B2 | 8/2009 | Gocke et al. |
| 7,651,838 B2 | 1/2010 | Paterlini-Brechot |
| 7,727,720 B2 | 6/2010 | Dhallan |
| 7,767,460 B2 | 8/2010 | Hunsley et al. |
| 8,304,187 B2 | 11/2012 | Fernando |
| 8,546,144 B2 | 10/2013 | Das et al. |
| 8,551,784 B2 | 10/2013 | Das et al. |
| 8,586,306 B2 | 11/2013 | Fernando |
| 8,841,077 B2 | 9/2014 | Paige et al. |
| 9,034,635 B2 | 5/2015 | Termaat et al. |
| 9,040,255 B2 | 5/2015 | Tsinberg et al. |
| 9,120,849 B2 | 9/2015 | Chiklis et al. |
| 9,127,048 B2 | 9/2015 | Chiklis et al. |
| 9,127,049 B2 | 9/2015 | Lanzavecchia et al. |
| 9,657,227 B2 | 5/2017 | Fernando |
| 9,926,590 B2 | 3/2018 | Fernando |
| 9,926,950 B2 | 3/2018 | Ooki et al. |
| 9,956,281 B2 | 5/2018 | Ryan et al. |
| 10,006,861 B2 | 6/2018 | Kreifels et al. |
| 10,091,984 B2 | 10/2018 | Fernando et al. |
| 10,144,955 B2 | 12/2018 | Fernando |
| 10,294,513 B2 | 5/2019 | Fernando |
| 2001/0018192 A1 | 8/2001 | Terstappen et al. |
| 2001/0049895 A1 | 12/2001 | Burke |
| 2001/0051341 A1 | 12/2001 | Lo et al. |
| 2002/0045196 A1 | 4/2002 | Mahoney et al. |
| 2002/0066216 A1 | 6/2002 | DeLaCruz |
| 2002/0086346 A1 | 7/2002 | Ryan |
| 2002/0119503 A1 | 8/2002 | Ryan et al. |
| 2003/0113705 A1 | 6/2003 | McMillian |
| 2003/0232377 A1 | 12/2003 | Thomas |
| 2004/0014107 A1 | 1/2004 | Garcia-Blanco et al. |
| 2004/0038424 A1 | 2/2004 | Maples |
| 2004/0137417 A1 | 7/2004 | Ryan |
| 2005/0029559 A9 | 2/2005 | Ahn et al. |
| 2005/0049793 A1 | 3/2005 | Paterlini-Brechot |
| 2005/0107316 A1 | 5/2005 | Strebhardt et al. |
| 2005/0164241 A1 | 7/2005 | Hahn et al. |
| 2005/0181353 A1 | 8/2005 | Rao et al. |
| 2005/0181463 A1 | 8/2005 | Rao et al. |
| 2005/0232377 A1 | 10/2005 | Kutz et al. |
| 2005/0277204 A1 | 12/2005 | Hollis et al. |
| 2006/0008807 A1 | 1/2006 | O'Hara et al. |
| 2006/0105372 A1 | 5/2006 | Bair et al. |
| 2006/0194192 A1 | 8/2006 | Rao et al. |
| 2006/0210429 A1 | 9/2006 | Hunsley et al. |
| 2007/0111233 A1 | 5/2007 | Bianchi et al. |
| 2007/0134658 A1 | 6/2007 | Bohmer |
| 2007/0178478 A1 | 8/2007 | Dhallan et al. |
| 2007/0202525 A1 | 8/2007 | Quake et al. |
| 2007/0243548 A1 | 10/2007 | Georges et al. |
| 2007/0243549 A1 | 10/2007 | Bischoff |
| 2007/0251337 A1 | 11/2007 | Reed et al. |
| 2007/0298406 A1 | 12/2007 | Martorell et al. |
| 2008/0020390 A1 | 1/2008 | Mitchell et al. |
| 2008/0057502 A1 | 3/2008 | Kopreski |
| 2008/0081689 A1 | 4/2008 | Seelig et al. |
| 2008/0096217 A1 | 4/2008 | Kopreski |
| 2008/0102470 A1 | 5/2008 | Dawson et al. |
| 2008/0108071 A1 | 5/2008 | Thompson |
| 2008/0119645 A1 | 5/2008 | Griffey et al. |
| 2008/0206866 A1 | 8/2008 | Zieglschmid et al. |

(56) References Cited

U.S. PATENT DOCUMENTS

| | | |
|---|---|---|
| 2008/0261292 A1 | 10/2008 | Kopreski |
| 2008/0318801 A1 | 12/2008 | Leung |
| 2009/0034446 A1 | 2/2009 | Adams et al. |
| 2009/0081678 A1 | 3/2009 | Ryan et al. |
| 2009/0197275 A1 | 8/2009 | Schoenbrunner et al. |
| 2009/0215036 A1 | 8/2009 | Stropp et al. |
| 2009/0308303 A1 | 12/2009 | Burlando |
| 2010/0167271 A1 | 7/2010 | Ryan |
| 2010/0184069 A1* | 7/2010 | Fernando ............ C12Q 1/6806 435/6.12 |
| 2010/0190796 A1 | 7/2010 | Verkman et al. |
| 2010/0209930 A1 | 8/2010 | Fernando |
| 2010/0216153 A1 | 8/2010 | Lapidus et al. |
| 2010/0317107 A1 | 12/2010 | Ryan |
| 2011/0027771 A1 | 2/2011 | Deng |
| 2011/0053208 A1 | 3/2011 | Reiss et al. |
| 2011/0110975 A1 | 5/2011 | Grunkemeyer et al. |
| 2011/0111410 A1 | 5/2011 | Ryan et al. |
| 2012/0164676 A1 | 6/2012 | Tsinberg et al. |
| 2012/0308990 A1 | 12/2012 | Termaat et al. |
| 2013/0034860 A1 | 2/2013 | Fernando |
| 2013/0209985 A1 | 8/2013 | Dudaronek et al. |
| 2014/0054508 A1 | 2/2014 | Fernando |
| 2014/0080112 A1 | 3/2014 | Ryan et al. |
| 2014/0199681 A1 | 7/2014 | Ryan et al. |
| 2014/0274740 A1* | 9/2014 | Srinivasan ........... C12Q 1/6855 506/2 |
| 2015/0030578 A1* | 1/2015 | Releford, Jr. .......... A61K 35/19 424/93.72 |
| 2015/0301037 A1 | 10/2015 | Tsinberg et al. |
| 2016/0143268 A1 | 5/2016 | Ryan |
| 2016/0174544 A1 | 6/2016 | Fernando et al. |
| 2016/0257995 A1 | 9/2016 | Qin et al. |
| 2017/0052173 A1 | 2/2017 | Hunsley et al. |
| 2017/0097361 A1 | 4/2017 | Alt et al. |
| 2017/0145475 A1 | 5/2017 | Qin et al. |
| 2018/0243406 A1 | 8/2018 | Ryan et al. |
| 2019/0127780 A1* | 5/2019 | Hunsley ................ C12Q 1/686 |
| 2019/0177774 A1 | 6/2019 | Connelly et al. |

FOREIGN PATENT DOCUMENTS

| | | |
|---|---|---|
| CN | 1665554 | 9/2005 |
| CN | 101148658 | 3/2008 |
| CN | 104634628 A | 5/2015 |
| CN | 107525818 A | 12/2017 |
| DE | 19928820 A1 | 12/2000 |
| EP | 1031626 A1 | 8/2000 |
| EP | 1207208 A2 | 5/2002 |
| EP | 1212613 A1 | 6/2002 |
| EP | 1217372 A1 | 6/2002 |
| EP | 1425294 A2 | 6/2004 |
| EP | 1816461 A1 | 8/2007 |
| EP | 1889921 A2 | 2/2008 |
| EP | 2216416 A1 | 8/2010 |
| EP | 2228453 A1 | 9/2010 |
| EP | 2411808 A2 | 2/2012 |
| EP | 2674502 A1 | 12/2013 |
| EP | 2704740 A2 | 3/2014 |
| EP | 2814981 A2 | 12/2014 |
| EP | 3118623 A1 | 1/2017 |
| EP | 3225699 A1 | 10/2017 |
| EP | 3572531 A1 | 11/2019 |
| JP | 4453999 B2 | 4/2010 |
| WO | 1990/10715 A1 | 9/1990 |
| WO | 93/05650 A1 | 4/1993 |
| WO | 94/02646 A1 | 2/1994 |
| WO | 95/26417 A1 | 10/1995 |
| WO | 1997/45729 A1 | 12/1997 |
| WO | 98/02528 A1 | 1/1998 |
| WO | 98/02740 A1 | 1/1998 |
| WO | 1998/44158 A1 | 10/1998 |
| WO | 98/59042 A1 | 12/1998 |
| WO | WO-1999/06594 A1 | 2/1999 |
| WO | 00/00813 A1 | 1/2000 |
| WO | 00/06780 A1 | 2/2000 |
| WO | 00/75647 A1 | 12/2000 |
| WO | 00/77235 A1 | 12/2000 |
| WO | 01/14872 A1 | 3/2001 |
| WO | 01/79851 A1 | 10/2001 |
| WO | 01/98542 A2 | 12/2001 |
| WO | 02/55985 A2 | 7/2002 |
| WO | 02/56030 A2 | 7/2002 |
| WO | 03/18757 A2 | 3/2003 |
| WO | 03/19141 A2 | 3/2003 |
| WO | 2003/35895 A2 | 5/2003 |
| WO | 03/69344 A1 | 8/2003 |
| WO | 2003/074723 A2 | 9/2003 |
| WO | 2003/74730 A1 | 9/2003 |
| WO | 03/95974 A2 | 11/2003 |
| WO | WO-2003/094990 | 11/2003 |
| WO | 2006/100063 A2 | 9/2006 |
| WO | 2007/022483 A2 | 2/2007 |
| WO | 2008/107724 A2 | 9/2008 |
| WO | 2008/111981 A1 | 9/2008 |
| WO | 2009/105499 A1 | 8/2009 |
| WO | 2010/078194 A1 | 7/2010 |
| WO | 2010/096323 A1 | 8/2010 |
| WO | 2010/111388 A2 | 9/2010 |
| WO | 2010/123908 A1 | 10/2010 |
| WO | 2010/132756 A2 | 11/2010 |
| WO | 2011/014741 A1 | 2/2011 |
| WO | 2011/057184 A1 | 5/2011 |
| WO | 2011/082415 A2 | 7/2011 |
| WO | 2012/145662 A1 | 10/2012 |
| WO | 2012/151391 A2 | 11/2012 |
| WO | 2012/166913 A1 | 12/2012 |
| WO | 2013/019290 A2 | 2/2013 |
| WO | 2013/086428 A1 | 6/2013 |
| WO | 2013/123030 A2 | 8/2013 |
| WO | 2014/029791 A1 | 2/2014 |
| WO | WO-2014/049022 A1 | 4/2014 |
| WO | 2015/134053 A1 | 9/2015 |
| WO | 2017/031354 A2 | 2/2017 |
| WO | 2017/201612 A1 | 11/2017 |
| WO | 2017/218789 A1 | 12/2017 |
| WO | 2018/022991 A1 | 2/2018 |
| WO | 2018/031903 A1 | 2/2018 |
| WO | 2018/035340 A1 | 2/2018 |
| WO | 2019/079743 A1 | 4/2019 |
| WO | 2019/090126 A1 | 5/2019 |
| WO | 2020/140035 A1 | 7/2020 |

OTHER PUBLICATIONS

Boddy et al., 2005. Prospective study of quantitation of plasma DNA levels in the diagnosis of malignant versus benign prostate disease. Clinical cancer research, 11(4), pp. 1394-1399. (Year: 2005).*
Chan et al., "Size Distributions of Maternal and Fetal DNA in Maternal Plasma", *Clinical Chemistry* (50:1) 88-92 (2004).
Chiu, et al., "Effects of Blood-Processing Protocols on Fetal and Total DNA Quantification in Maternal Plasma", *Clinical Chemistry* (47:9) 1607-1613 (2001).
Fan et al., "Analysis of the Size Distributions of Fetal and Maternal Cell-Free DNA by Paired-End Sequencing", *Clinical Chemistry* (56:8) 1279-1286 (2010).
Lo et al., "Noninvasive Prenatal Diagnosis of Fetal Chromosomal Aneuploidies by Maternal Plasma Nucleic Acid Analysis," Clinical Chemistry 54(3):461-466 (2008).
Lo et al., "Presence of fetal DNA in maternal plasma and serum," The Lancet 350:485-487 (1997).
Norton et al., "A New Blood Collection Device Minimizes Cellular DNA Release During Sample Storage and Shipping When Compared to a Standard Device", *Journal of Clinical Laboratory Analysis* (27) 305-311 (2013).
Barra et al., "EDTA-mediated inhibition of DNases protects circulating cell-free DNA from ex vivo degradation in blood samples," Clinical Biochemistry 48:976-81 (2015).

(56) References Cited

OTHER PUBLICATIONS

Dharajiya et al., "Noninvasive Prenatal Testing Using Cell-Free Fetal DNA in Maternal Plasma," Curr Protoc Hum Genet. 84:8.15.1, 2 pages (2015).
Fleischhacker et al., "Methods for isolation of cell-free plasma DNA strongly affect DNA yield," Clinica Chimica Acta 412:2085-2088 (2011).
Fomovsky et al., "Centrifuge-free isolation of liquid plasma from clinical samples from whole blood" (2012).
Lambert et al., "Male microchimerism in healthy women and women with scleroderma: cells or circulating DNA? A quantitative answer," Blood 100(8):2845-2851 (2002).
Lo et al., "Rapid clearance of Fetal DNA from Maternal Plasma," Am. J. Hum. Genet. 64:218-224 (1999).
Lo et al., "Prenatal diagnosis: progress through plasma nucleic acids," Nature Reviews Genetics 8:71-77 (2007).
Lo et al., "Prenatal Diagnosis of Fetal RhD Status by Molecular Analysis of Maternal Plasma," N Engl J Med 1734-1738 (1998).
Lo et al., "Quantitative Analysis of Fetal DNA in Maternal Plasma and Serum: Implications for Noninvasive Prenatal Diagnosis," Am. J. Hum. Genet. 62:768-775 (1998).
Wong et al., "Optimizing blood collection, transport and storage conditions for cell free DNA increases access to prenatal testing," Clinical Biochemistry 46:1099-1104 (2013).
"Cell-Free DNA Collection Tube" Roche (2016).
Ashoor et al., "Fetal fraction in maternal plasma cell-free DNA at 11-13 weeks' gestation: relation to maternal and fetal characteristics," Ultrasound Obstet Gynecol 41:26-32 (2013).
Bergholtz, "Confirmation of Equivalence of One-Spin and Two-Spin Protocols for Plasma Isolation from LBgard® Blood Tubes," Biomatrica (Sep. 2018).
Bevilacqua et al., "Performance of screening for aneuploidies by cell-free DNA analysis of maternal blood in twin pregnancies," Ultrasound Obstet Gynecol 45:61-66 (2015).
Harmony Prenatal Test—IVD Kit—P/N 08011281001 (FGK1002)—Instructions for Use, 31 pages. (Retrieved from the internet on or around Jul. 17, 2018).
Juneau et al., "Microarray-Based Cell-Free DNA Analysis Improves Noninvasive Prenatal Testing," Fetal Diagnosis and Therapy, 36:282-286 (2014).
Norton et al., "Non-Invasive Chromosomal Evaluation (NICE) Study: results of a multicenter prospective cohort study for detection of fetal trisomy 21 and trisomy 18," American Journal of Obstetrics & Gynecology 137.e1, 8 pages (2012).
Norton et al., "Cell-free DNA Analysis for Noninvasive Examination of Trisomy," The New England Journal of Medicine, 372(17):1589-97 (2015).
Qin et al., "Evaluation of a Single Spin Protocol for Plasma DNA Isolation from Blood Collected & Stored in Cell-Free DNA BCT," Annual Meeting of American College of Medical Genetics and Genomics (Mar. 2016).
Roche Product Alert Notice—AA-Harmony Test-QN-SEQ-2017-003 (2017).
Sparks et al., "Noninvasive prenatal detection and selective analysis of cell-free DNA obtained from maternal blood: evaluation for trisomy 21 and trisomy 18," American Journal of Obstetrics & Gynecology 319.e1, 9 pages (2012).
Sparks et al., "Selective analysis of cell-free DNA in maternal blood for evaluation of fetal trisomy," Prenatal Diagnosis 32:3-9 (2012).
Stokowski et al., "Evaluation of Automated Cell-Free DNA Extraction Methods with the Harmony® Prenatal Test," Roche Sequencing Solutions, Roche Diagnostics, Inc. (2018).
Strom et al., "Improving the Positive Predictive Value of Non-Invasive Prenatal Screening (NIPS)," PLOS One, 18 pages (2017).
Niel et al., Shedding light on the cell biology of extracellular vesicles, Nat. Rev. Mol. Cell Biol., 19(4):213-228 (2018).
Notice of Opposition to a European patent dated Apr. 24, 2019, received from the European Patent Office Application No. 02761478.3.

Novaro, American Association for Cancer Research; 93rd Annual Meeting; Apr. 6-10, 2002; San Francisco, California; 43 (2002).
Oh et al., Damage to red blood cells during whole blood storage, J. Trauma Acute Care Surg., 89(2):344-350 (2020).
Ohtani et al., Differential effects of alpha-, beta-and gamma-cyclodextrins on human erythrocytes, Eur. J. Biochem., 186(1-2):17-22 (1989).
Ono et al., Circulating microRNA Biomarkers as Liquid Biopsy for Cancer Patients: Pros and Cons of Current Assays, Journal of clinical medicine, 4(10):1890-907 (2015).
Opinion Concerning the Determination of Certain Formaldehyde Releasers in Cosmetic Products. The Scientific Committee on Cosmetic Product and Non-Food Products intended for Consumers, 1-9 (2002).
Palmer et al., Flow cytometric determination of residual white blood cell levels in preserved samples from Teukoreduced blood products, Transfusion, 48(1):118-128 (2008).
Pan et al., Cell-free Fetal DNA Levels in Pregnancies Conceived by PIP, Human Reproduction, 20(11):3152-3156 (2005).
Passage from confidential document, Streck, Inc. Cell-Free DNA BCT 510(k) Premarket Notification, Sep. 19, 2012.
Perakis et al., Emerging concepts in liquid biopsies, BMC Med., 15(1):75 (2017).
Persico et al., Cell-free DNA testing in the maternal blood in high-risk pregnancies after first trimester combined screening, Prenatal Diagnosis, 36(3):232-6 (2016).
Pertl et al., Fetal DNA in Maternal Plasma: Emerging Clinical Applications, by The American College of Obstetricians and Gynecologists, 98:483-490 (2001).
Pinzani et al., Circulating nucleic acids in cancer and pregnancy, Methods: A Companion to Methods in Enzymology, 40(4):302-307 (2010).
Punnoose et al., PTEN loss in circulating tumour cells correlates with PTEN loss in fresh tumour tissue from castration-resistant prostate cancer patients, British Journal of Cancer, 113(8):1225-33 (2015).
Puren et al., Laboratory operations, specimen processing, and handling for viral load testing and surveillance, Journal of Infectious Diseases, 201(supp 1):S27-S36 (2010).
Quezada et al., Fetal fraction of cell-free DNA in maternal plasma in the prediction of spontaneous preterm delivery, Ultrasound in Obstetrics & Gynecology, 45(1):101-5 (2015).
Quezada et al., Screening for trisomies 21; 18 and 13 by cell-free DNA analysis of maternal blood at 10-11 weeks' gestation and the combined test at 11-13 weeks, Ultrasound in Obstetrics & Gynecology, 45(1):36-41 (2015).
Rait et al., Conversions of formaldehyde-modified 2'-deoxyadenosine 5'-monophosphate in conditions modeling formalin-fixed tissue dehydration, J. Histochem Cytochem 54(3):301-310 (2006).
Rajewski et al., Pharmaceutical applications of cyclodextrins. 2. In vivo drug delivery, J. Pharm. Sci., 85(11):1142-1169 (1996).
Ramirez et al., Technical challenges of working with extracellular vesicles, Nanoscale, 10:881-906 (2018).
Raposo et al., Extracellular vesicles: exosomes, microvesicles, and friends, J. Cell Biol., 200(4):373-83 (2013).
Risberg, Establishment of PCR based methods for detection of ctDNA in blood, Thesis submitted for the Master's degree in Biomedicine. Oslo University Hospital, Institute for Cancer Research, Department of Genetics and Oslo and Akershus University College of Applied Sciences, (2013).
Róka et al., Evaluation of the cytotoxicity of (Alpha)-cyclodextrin derivatives on the caco-2 cell line and human erythrocytes, molecules, 20(11):20269-85 (2015).
Ruiz et al., Limited genomic heterogeneity of circulating melanoma cells in advanced stage patients, Physical Biology, 12(1):016008 (2015).
Rykova et al., Concentrations of Circulating RNA from Healthy Donors and Cancer Patients Estimated by Different Method, Ann. N.Y. Acad Sci., 1075:328-333 (2006).
Salvianti et al., Single circulating tumor cell sequencing as an advanced tool in cancer management, Expert review of molecular diagnostics, 27:1-3 (2015).

(56) References Cited

OTHER PUBLICATIONS

Salvianti et al., The pre-analytical phase of the liquid biopsy, N. Biotechnol., 55:19-29 (2020).
Samango-Sprouse et al., SNP-based non-invasive prenatal testing detects sex chromosome aneuploidies with high accuracy, Prenatal diagnosis, 33(7):643-9 (2013).
Samoila et al., Method development and validation for clinical cfDNA extraction from blood, InASCO Annual Meeting Proceedings, 33(15_suppl):e22185 (2015).
Samuel et al., The effect of chorionic villus sampling on the fraction of cell-free fetal DNA in maternal plasma, The Journal of Maternal-Fetal & Neonatal Medicine, 15:1-4 (2015).
Schatz et al., Preservation of Cell-Free DNA in Stored Blood Samples for the Analysis of the (M) Sept9 Colorectal Cancer Screening Marker Enables Sample Shipment by Mail, Published as a poser at the conference on International federation of clinical chemistry and laboratory medicine Worldlab and EU, Berlin, Germany (2011).
Scheffer et al., Noninvasive fetal blood group genotyping of rhesus D, c, E and of K in alloimmunised pregnant women: evaluation of a 7-year clinical experience, BJOG: An International Journal of Obstetrics & Gynaecology, 118(11):1340-8 (2011).
Schiavon et al., Analysis of ESR1 mutation in circulating tumor DNA demonstrates evolution during therapy for metastatic breast cancer, Science translational medicine, 7(313):313ra182 (2015).
Sekizawa et al., Apoptosis in Fetal Nucleated Erythrocytes Circulating in Maternal Blood, Prenatal Diagnosis, 20:886-889 (2000).
Seo et al., An Experience of Using the Harmony Test for Genomics-Based Non-Invasive Prenatal Testing, Journal of Laboratory Medicine and Quality Assurance, 37(1):44-6 (2015).
Shi et al., Feasibility of noninvasive prenatal testing for common fetal aneuploidies in an early gestational window, Clinica. Chimica. Acta., 439:24-8 (2015).
Sigma-Aldrich, 1-Aza-3,7-dioxabieyclo[3.3.0]octane-5-methanol solution, Available online at <www.sigmaaldrich.com/catalog/product/aldrich/417807?lang=en%region=US>, 5 pages, Accessed Jan. 13, 14.
Sillence et al., Fetal Sex and RHD Genotyping with Digital PCR Demonstrates Greater Sensitivity than Real-time PCR, Clinical Chemistry, 61(11):1399-407 (2015).
Skidmore et al., Characterization and Use of the Potent Ribonuclease Inhibitor Aurintricarboxylic Acid for the Isolation of RNA from Animal Tissues, Biochem Journal, 263(1): 73-80 (1989).
Slocum et al., Electron-Microscopic Cytochemical Localization of Diamine and polyamine oxidases in Pea and Maize Tissues, Planta., 183:443-450 (1991).
Smid et al., Evaluation of Different Approaches for Fetal DNA Analysis from Maternal Plasma and Nucleated Blood Cells, Technical Briefs, 45(9):1570-1572 (1999).
Smid et al., Quantitative Analysis of Fetal DNA in Maternal Plasma in Pathological Conditions Associated with Placental Abnormalities, Annals New York Academy of Sciences, 951:133-137 (2001).
Smit et al., Semiautomated DNA Mutation Analysis Using a Robotic Workstation and Molecular Beacons, Clinical Chemistry, 47:739-744 (2001).
Song et al., Non-invasive prenatal testing for fetal aneuploidies in the first trimester of pregnancy, Ultrasound in Obstetrics & Gynecology, 45(1):55-60 (2015).
Stokowski et al., Clinical performance of non-invasive prenatal testing (NIPT) using targeted cell-free DNA analysis in maternal plasma with microarrays or next generation sequencing (NGS) is consistent across multiple controlled clinical studies, Prenatal Diagnosis, 35(12):1243-6 (2015).
Streck et al., 1-XP55419765A, Product Summary: Cell-Free DNA(Trademark) BCT, (2009).
Stumm et al., Diagnostic accuracy of random massively parallel sequencing for non-invasive prenatal detection of common autosomal aneuploidies: a collaborative study in Europe, Prenatal Diagnosis, 34(2):185-91 (2014).
Su et al., Detection of a K-ras mutation in urine of patients with colorectal cancer, Cancer Biomarkers, 1(2-3):177-82 (2005).
Swarup et al., Circulating (cell-free) Nucleic Acids—A Promising, Non-invasive Tool for Early Detection of Several Human Diseases, FEBS Letters, 481:795-799 (2007).
Alvarez et al., Comparison of protein, microRNA, and mRNA yields using different methods of urinary exosome isolation for the discovery of kidney disease biomarkers, Kidney International 82:1024-1032 (2012).
Ames et al., An Appraisal of the "Vacutainer" System for Blood Collection, Ann. Clin. Biochem., 12:151-155 (1975).
Angert et al., Fetal Cell-free Plasma DNA Concentrations in Maternal Blood Are Stable 24 Hours after Collection Analysis of First-and Third-Trimester Samples, Clinical-Chemistry, 49(1):195-198 (2003).
Arikan, A comparison of the effect of methyl-beta-cyclodextrin on the osmotic fragility of ovine, bovine and human erythrocytes, Turk J. Vet. Anim. Sci., 27:383-387 (2003).
Ashoor et al., Trisomy 13 detection in the first trimester of pregnancy using a chromosome-selective cell-free DNA analysis method, Ultrasound in Obstetrics & Gynecology, 41 (1):21-5 (2012).
Barrett et al., Implementing Prenatal Diagnosis Based on Cell-Free Fetal DNA. Accurate Identification of Factors Affecting Fetal DNA Yield, PLoS One, 6(10):e25202 (2011).
Bayindir et al., Noninvasive Prenatal Testing Using a Novel Analysis Pipeline to Screen for All Autosomal Fetal Aneuploidies Improves Pregnancy Management, European Journal of Human Genetics, 23(10): 1286-93 (2015).
Beck et al., Digital Droplet PCR for Rapid Quantification of Donor DNA in the Circulation of Transplant Recipients as a Potential Universal Biomarker of Graft Injury, Clinical chemistry, 59(12):1732-41 (2013).
Benachi et al., Cell-Free DNA Analysis in Maternal Plasma in Cases of Fetal Abnormalities Detected on Ultrasound Examination, Obstetrics & Gynecology, 125(6): 1330-7 (2015).
Bethel et al., Fluid phase biopsy for detection and characterization of circulating endothelial cells in myocardial infarction, Physical biology, 11(1):016002 (2014).
Bevilacqua et al., Performance of screening for aneuploidies by cell-free DNA analysis of maternal blood in twin pregnancies, Ultrasound in Obstetrics & Gynecology, 45(1):61-6 (2015).
Bianchi et al., DNA sequencing versus standard prenatal aneuploidy screening, New England Journal of Medicine, 370(9):799-808 (2014).
Bianchi et al., Fetal sex chromosome testing by maternal plasma DNA sequencing: clinical laboratory experience and biology, Obstetrics & Gynecology, 125(2):375-82 (2015).
Bianchi et al., PCR Quantifications of Fetal Cells in Maternal Blood in Normal and Aneuploid Pregnancies, Am. J. Hum. Genet., 61:822-29 (1997).
Bianchi, Invited Editorial Fetal DNA in Maternal Plasma: The Plot Thickens and the Placental Barrier Thins, by The American Society of Human Genetics, 62:763-764 (1998).
Bina-Stein et al., Aurintricarboxylic Acid Is a Nonspecific Enzyme Inhibitor, Department of Chemistry, Yak University, New Haven, Connecticut, 12:191-193 (1975).
Biocept (BIOC) Announces Patent for Blood Collection and Transport Tube; StreetInsider.com; http://www.streetinsider.com/corporate+news/biocept+(BIOC)+Announces; (2015).
Biocept—Expands Patent Protection for Liquid Biopsy Platform http://ir.biocept.com/releasedetail.cfm?releaseID=915635(2015).
Biocept Completing the Answer; http://ir.biocept.com/secfiling.cfm?filingid=1193125-15-16425%cik=1044378. (2015).
Botezatu et al., Genetic Analysis of DNA Excreted in Urine: A New Approach for Detecting Specific Genomic DNA Sequences from Cells Dying in an Organism, Clinical Chemistry, 46(8):1078-1084 (2000).
Brar et al., The fetal fraction of cell-free DNA in maternal plasma is not affected by a priori risk of fetal trisomy, The Journal of Maternal-Fetal & Neonatal Medicine, 26(2):143-5 (2013).
Brown, Effect of Blood Collection and Processing on Radioimmunoassay Results for Apolipoprotein B in Plasma, Clinical Chemistry, 36(9): 1662-1666 (1990).
Bruno et al., Use of copy number deletion polymorphisms to assess DNA chimerism, Clinical chemistry, 60(8):1105-14 (2014).

(56) References Cited

OTHER PUBLICATIONS

Butler, Genetics and Genomics of Core Short Tandem Repeat Loci Using in Human Identity Testing, Journal of Forensic Science, 51(2):253-265 (2006).
Buysse et al., Reliable noninvasive prenatal testing by massively parallel sequencing of circulating cell-free DNA from maternal plasma processed up to 24h after venipuncture, Clinical biochemistry, 46(18):1783-6 (2013).
Cannas et al., Implications of storing urinary DNA from different populations for molecular analyses, PloS one, 4(9):e6985 (2009).
Carlsson et al., Circulating Tumor Microemboli Diagnostics for Patients with Non-Small-Cell Lung Cancer, Journal of Thoracic Oncology, 9(8):1111-9 (2014).
Chan et al., Hypermethylated RASSFIA in maternal Plasma: A Universal Fetal DNA Marker that Improves the Reliability of Noninvasive Prenatal Diagnosis, Clinical Chemistry, 52(12):2211-2218 (2006).
Cherepanova et al., Immunochemical assay for deoxyribonuclease activity in body fluids, Journal of immunological methods, 325(1):96-103 (2007).
Chinnapapagari et al., Treatment of maternal blood samples with formaldehyde does not alter the proportion of circulatory fetal nucleic acids (DNA and mRNA) in maternal plasma, Clin Chem., 51(3):652-5 (2005).
Chudziak et al., Clinical evaluation of a novel microfluidic device for epitope-independent enrichment of circulating tumour cells in patients with small cell lung cancer, The Analyst, 141(2):669-78 (2015).
Chung et al., Detrimental Effect of Formaldehyde on Plasma RNA Detection, Clin. Chem., 51(6):1074-6 (2005).
Chung et al., Lack of Dramatic Enrichment of Fetal DNA in Maternal Plasma by Formaldehyde Treatment, Clinical Chemistry, 51(3):655-8 (2005).
Chutkan et al., Quantitative and qualitative preparations of bacterial outer membrane vesicles, Methods Mol. Biol., 966:259-272 (2013).
Clark-Ganheart et al., Use of Cell-Free DNA in the Investigation of Intrauterine Fetal Demise and Miscarriage, Obstetrics & Gynecology, 125(6):1321-9 (2015).
Clinical Applications of Flow Cytometry: Immunophenotyping of Leukemic Cells; Approved Guideline; NCCLS, 18(8) (1998).
Colombo et al., Biogenesis, secretion, and intercellular interactions of exosomes and other extracellular vesicles, Annu. Rev. Cell Dev. Biol., 30:255-89 (2014).
Comas et al., Initial Experience with Non-Invasive Prenatal Testing of Cell-Free DNA for Major Chromosomal Anomalies in a Clinical Setting, The Journal of Maternal-Fetal & Neonatal Medicine, 28(10):1-6 (2014).
Costa et al., Fetal Expressed Gene Analysis in maternal Blood: A New Tool for Noninvasive Study of the Fetus, Clinical Chemistry, 49(6):981-983 (2003).
Curnow et al., Detection of Triploid, Molar, and Vanishing Twin Pregnancies by a Single-Nucleotide Polymorphism-Based Noninvasive Prenatal Test, American Journal of Obstetrics and Gynecology, 212(1):79.e1-9 (2015).
Das et al.,, Effects of a novel cell stabilizing reagent on DNA amplification by PCR as compared to traditional stabilizing reagents, Acta Histochemica; 116(1):55-60 (2014).
Dash et al., Using Noninvasive Prenatal Testing for Aneuploidies in a Developing Country: Lessons Learnt, Journal of Fetal Medicine, 1(3):131-5 (2014).
De Miranda et al., Cyclodextrins and ternary complexes: technology to improve solubility of poorly soluble drugs, Br. J. Pharm. Sci., 47(4):665-81 (2011).
Dean et al., Comprehensive human genome amplification using multiple displacement amplification, Pro. Nat. Acad. Sci., 99(8):5261-5266 (2002).
Deatherage et al., Membrane Vesicle Release in Bacteria, Eukaryotes, and Archaea: a Conserved yet Underappreciated Aspect of Microbial Life, Infection and Immunity, 80(6):1948-1957 (2012).
Denis et al., Efficient Detection of BRAF Mutation in Plasma of Patients after Long-term Storage of Blood in Cell-Free DNA Blood Collection Tubes, Clinical Chemistry, 61(6):886-8 (2015).
Dhallan et al., A noninvasive test for prenatal diagnosis based on fetal DNA present in maternal blood: a preliminary study, The Lancet.; 369 (9560): 474-481 (2007).
Dhallan et al., Methods to Increase the Percentage of Free Fetal DNA Recovered from the Maternal Circulation, JAMA, 291(9):1114-1119 (2004).
Diamond et al., Diverse and Targetable Kinase Alterations Drive Histiocytic Neoplasms, Cancer discovery, 6(2):154-65 (2016).
Ding, et al., MS Analysis of Single-Nucleotide, Differences in Circulating Nucleic Acids: Application to Noninvasive Prenatal Diagnosis, Proc. Natl. Acad Sci. USA, 101:10762-10767 (2004).
Dumaswala et al., Improved red blood cell preservation correlates with decreased loss of bands 3, 4.1, acetylcholinestrase, and lipids in microvesicles, Blood, 87(4):1612-6 (1996).
EP Application No. 10000518.0 (Patent No. EP2228453), Brief communication regarding Letter from the opponent 02 (Cenata) of Jun. 6, 2018 including exhibits, dated Jun. 14, 2018.
EP Application No. 10000518.0 (Patent No. EP2228453), Brief communication to Opponent 1 and Opponent 2 dated May 29, 2018 and Reply including exhibits of patent proprietor to notice(s) of opposition dated Apr. 26, 2018.
European application No. 03 256 535.0-2113, Decision to refuse a European Patent application, dated May 30, 2007.
European Application No. 10000518.0, Communication of a notice of intervention including exhibits by Cenata GmbH, dated Apr. 13, 2018.
European Application No. 10000518.0, Communication of a notice of opposition including exhibits, dated Sep. 12, 2017.
European Application No. 10704474.5, European Patent Office Summons to Attend, dated Jan. 27, 2016.
European Application No. 10704474.5, European Third Party Observations, dated Aug. 30, 2016.
European Application No. 13706856.5, European Communication of a notice of opposition including exhibits, dated Mar. 28, 2018.
European Application No. 13706856.5, European Third Party Observations, dated May 25, 2016.
European Application No. 16199783, European Search Report and Opinion, dated Feb. 17, 2017.
European Application No. 19186944, European Search Report and Opinion, dated Oct. 17, 2019.
European Application No. EP 17 84 2131 , Supplementary partial search report, dated Mar. 16, 2020.
Fairbrother et al., Clinical experience of noninvasive prenatal testing with cell-free DNA for fetal trisomies 21, 18, and 13, in a general screening population, Prenatal Diagnosis, 33(6):580-3 (2013).
Fernando et al., A new methodology to preserve the original proportion and integrity of cell-free fetal DNA in maternal plasma during sample processing and storage, 30(5):418-424 (2010).
Fernando et al., Stabilization of cell-free RNA in blood samples using a new collection device, Clinical Biochemistry, 45(16-17):1497-1502 (2012).
Fernando et al., Stabilization of cell-free RNA in plasma for noninvasive diagnosis and prognosis, retrieved from the internet: URL http://www.streck.com/resources/cell_stabilization/cell-free_RNA_BCT_Stabilization_of_Cell-Free_RNA_in_Plasma.pdf(2010).
Funasaki et al., Mechanisms and surface chemical prediction of imipramine-induced hemolysis suppressed by modified cyclodextrins, J. Pharm. Sci., 90(8):1056-65 (2001).
Futch et al., Initial clinical laboratory experience in noninvasive prenatal testing for fetal aneuploidy from maternal plasma DNA samples, Prenatal Diagnosis, 33(6):569-74 (2013).
Gheinani et al., Improved isolation strategies to increase the yield and purity of human urinary exosomes for biomarker discovery, Scientific Reports, 8:3945 (2018).
Gielis et al., Cell-Free DNA: An Upcoming Biomarker in Transplantation, Am. J. Transplant., 15(10):2541-51 (2015).
Gil et al., Cell-free DNA analysis for trisomy risk assessment in first-trimester twin pregnancies, Fetal Diagnosis and Therapy, 35(3):204-11 (2013).

(56) References Cited

OTHER PUBLICATIONS

Gil et al., Implementation of maternal blood cell-free DNA testing in early screening for aneuploidies, Ultrasound in Obstetrics & Gynecology, 42(1):34-40 (2013).
Gil et al., UK NHS pilot study on cell-free DNA testing in screening for fetal trisomies: factors affecting uptake, Ultrasound in Obstetrics & Gynecology, 45(1):67-73 (2015).
Gonzales et al., Application of Fetal. DNA Detection in Maternal Plasma: A Prenatal Diagnosis Unit Experience, Journal of Histochemistry & Cytochemistry, 53(3):307-314 (2005).
Greenwalt et al., Erythrocyte membrane vesiculation and changes in membrane composition during storage in citrate-phosphate-dextrose-adenine-1, Vox Sang., 47(4):261-70 (1984).
Grölz et al., Liquid biopsy preservation solutions for standardized pre-analytical workflows-venous whole blood and plasma, Curr. Pathobiol. Rep., 6(4):275-286 (2018).
Grömminger et al., Fetal aneuploidy detection by cell-free DNA sequencing for multiple pregnancies and quality issues with vanishing twins, Journal of Clinical Medicine, 3(3):679-92 (2014).
Gross et al., Rapid changes in circulating tumor cells following anti-angiogenic therapy, Convergent Science Physical Oncology, 1(1):015002 (2015).
György et al., Improved circulating microparticle analysis in acid-citrate dextrose (ACD) anticoagulant tube, Thromb Res., 133(2):285-92 (2014).
Haaland, Molecules and models: the molecular structures of main group element compounds Oxford University Press, (abstract available at http://www.oxfordscholarship.com/view/10.1093/acprof:oso/9780199235353.001.0001/acprof-9780199235353-chapter-12) (2018).
Hallick et al., Use of Aurintricarboxylic Acid as in Inhibitor of Nucleases During Nucleic Acid Isolation, Nucleic Acid Research, 4:3055-3064 (1977).
Hanessian et al., The Synthesis of functionalized cyclodextrins as scaffolds and templates for molecular diversity, Catalysis, and Inclusion Phenomena, J. Org. Chem., 60(15):4786-4797 (1995).
Hidestrand et al., Influence of temperature during transportation on cell-free DNA analysis, Fetal diagnosis and Therapy, 31(2):122-8 (2012).
Hindson et al., High-throughput droplet digital PCR system for absolute quantitation of DNA copy number, Analytical Chemistry, 83(22):8604-10 (2011).
Holford et al., Stability of beta-actin mRNA in plasma, Annals of the New York Academy of Science, 1137:108-111 (2008).
Holmberg et al., Akonni TruTip(®) and Qiagen(®) methods for extraction of fetal circulating DNA-evaluation by real-time and digital PCR, PloS One, 8(8):e73068 (2013).
Hooks et al., Non-invasive risk assessment of fetal sex chromosome aneuploidy through directed analysis and incorporation of fetal fraction, Prenatal Diagnosis, 34(5):496-9 (2014).
Hynek et al., MoM-based Approach to Noninvasive Prenatal Testing Using Exponentially Weighted. Moving Average Chart and Chromosomal Fingerprint, International Journal of Biomedicine and Healthcare, 3(2):12-15 (2015).
Ignatiadis et al.. Circulating Tumor Cells and Circulating Tumor DNA: Challenges and Opportunities on the Path to Clinical Utility, Clinical. Cancer Research, 21(21):4786-800 (2015).
International Application No. PCT/US2018/056747, International Search Report and Written Opinion, dated Dec. 17, 2018.
International Application No. PCT/US2018/056747, International Preliminary Reporton Patentability, dated Apr. 30, 2020.
International Application No. PCT/US2010/023859, International Search Report and Written Opinion, filed Feb. 11, 2010.
International Application No. PCT/US2010/55815, International Search Report and Written Opinion, filed Nov. 8, 2010.
International Application No. PCT/US2013/025912, International Preliminary Report on Patentability, dated Apr. 25, 2014.
International Application No. PCT/US2013/025912, Written Opinion of the International Preliminary Examining Authority, dated Jan. 24, 2014.
International Application No. PCT/US2014/047551, International Preliminary Report on Patentability, dated Dec. 10, 2015.
International Application No. PCT/US2014/047551, International Search Report & Written Opinion, dated Oct. 23, 2014.
Irie et al., Cyclodextrin-induced hemolysis and shape changes of human erythrocytes in vitro, J. Pharmacobiodyn, 5(9):741-744(1982).
Ishizawa et al., Simple procedure of DNA isolation from human serum, Nucleic Acids Research, 19(20):5792 (1991).
Szarvas et al., Determination of Endogenous Formaldehyde Level in Human Blood and Urine by Dimedone-14C Radiometric Method, J. Radioanal. Nucl. Chem., Letters; 106, 357-367 (1986).
Takabayashi et al., Development of Non-invasive Fetal DNA Diagnosis from Maternal Blood, Prenatal Diagnosis, 15:74-77 (1995).
Thung et al., Implementation of whole genome massively parallel sequencing for noninvasive prenatal testing in Taboratories, Expert Review of Molecular Diagnostics, 15(1):111-24 (2015).
Tong et al., Diagnostic developments involving cell-free (circulating) nucleic acids, Clinica. Chimica. Acta., 363(1):187-96 (2006).
Toro et al., Comparison of cell stabilizing blood collection tubes for circulating plasma tumor DNA, Clinical Biochemistry, 48(15):993-8 (2015).
Toro, Detection of PIK3CA Mutations in Plasma Tumor DNA Circulating in Peripheral Blood of Breast Cancer Patients, Thesis submitted for the degree of Master of Science in Molecular and Cellular Biology. Johns Hopkins University, Baltimore, Maryland (2014).
Torrano et al., Vesicle-MaNiA: extracellular vesicles in liquid biopsy and cancer, Curr. Opin. Pharmacol., 29:47-53 (2016).
Tynan et al., Application of risk score analysis to low-coverage whole genome sequencing data for the noninvasive detection of trisomy 21, trisomy 18, and trisomy 13, Prenatal diagnosis, 36(1):56-62 (2016).
U.S. Provisional Application filed Feb. 3, 2017, by Noble et al., U.S. Appl. No. 62/454,451.
U.S. Provisional Application filed Feb. 3, 2017, by Noble et al., U.S. Appl. No. 62/454,460.
Uekama et al., Protective effects of cyclodextrins on drug-induced hemolysis in vitro, J. Pharmacobiodyn., 4(2):142-4 K1981).
U.S. FDA, Draft Guidance for Industry: Pre-Storage Leukocyte Reduction of Whole Blood and Blood Components Intended for Transfusion, Vaccines, Blood & Biologies, available at www.fda.gov/biologicsbloodvaccines/guidancecomplianceregulatoryinformation/guidance/blood/ucm076769.htm (2011).
Vandenberghe et al., Non-invasive detection of genomic imbalances in Hodgkin/Reed-Sternberg cells in early and advanced stage Hodgkin's lymphoma by sequencing of circulating cell-free DNA: a technical proof-of-principle study, The Lancet Haematology, 2(2):e55-65 (2015).
Verweij et al., European Non-lnvasive Trisomy Evaluation (EU-NITE) study: a multicenter prospective cohort study for non-invasive fetal trisomy 21 testing, Prenatal Diagnosis, 33(10):996-1001 (2013).
Vu et al., Genotyping for DQAI and PM loci in urine using PCR-based amplification: Effects of sample volume storage temperature, preservatives, and aging on DNA extraction and typing, Forensic Science International, 102(1):23-34 (1999).
Wagner, Free DNA—new potential analyte in clinical laboratory diagnostics, Biochem Med (Zagreb), 22(1):24-38 (2012).
Wang et al., Gestational age and maternal weight effects on fetal cell-free DNA in maternal plasma, Prenatal diagnosis, 33(7):662-6 (2013).
Wang et al., Exploring Glycan Markers for Immunotyping and Precision-targeting of Breast Circulating Tumor Cells, Archives of medical research, 46(8):642-50 (2015).
Wang et al., Lipoprotient Lipase: from gene to obesity, Am. J. Physiol. Endocrinol. Met., 297(2):E271-E288 (2009).
Wang et al., Maternal mosaicism is a significant contributor to discordant sex chromosomal aneuploidies associated with noninvasive prenatal testing, Clinical chemistry, 60(1):251-9 (2014).
Wang et al., Real-time PCR evaluation of cell-free DNA subjected to various storage and shipping conditions, Genetics and Molecular Research, 14(4):12797-804 (2015).

(56) References Cited

OTHER PUBLICATIONS

Wang et al., Sensitive detection of mono-and polyclonal ESR1 mutations in primary tumors, metastatic lesions and cell free DNA of breast cancer patients, Clinical Cancer Research, 22(5):1130-7 (2016).
Weisz et al., Protection of erythrocytes against hemolytic agents by cyclodextrin polysulfate, Biochem Pharmacol., 45(5):1011-6 (1993).
Werner et al., Analytical Validation and Capabilities of the Epic CTC Platform: Enrichment-Free Circulating Tumour Cell Detection and Characterization, Journal of Circulating Biomarkers, 4:3 (2015).
What are the regulatory Definitions for "Ambient", "Room Temperature" and "Cold Chain" (https://www.gmp-compliance.org/gmp-news/what-are-the-regulatory-definitions-for-ambient-room-temperature-and-cold-chain) (2017).
Wiebe et al., Inhibition of Cell Proliferation by Glycerol, Life Sciences, 48(16)1511-7 (1991).
Wienzek-Lischka et al., Noninvasive fetal genotyping of human platelet antigen-1a using targeted massively parallel sequencing, Transfusion, 55(6 Pt 2):1538-44 (2015).
Willems et al., The first 3,000 non-invasi-s7e prenatal tests (NWT) with the harmony test in Belgium and the Netherlands, Facts, Views & Vision in ObGyn, 6(1):7-12 (2014).
Wolf, The nature and significance of platelet products in human plasma, Br. J. Haematol., 13(3):269-88 (1967).
Wong et al., The role of physical stabilization in whole blood preservation, Sci. Rep., 6:21023 (2016).
Woolcock et al., Noninvasive prenatal testing, Australian Family Physician, 43(7):432-4 (2014).
Yoshida et al., Red blood cell storage lesion: causes and potential clinical consequences, Blood Transfus., 17(1):27-52 (2019).
Zhang et al., Effect of Formaldehyde Treatment on the Recovery of Cell-Free Fetal DNA from Maternal Plasma at Different Processing Times, Clinica Chimica Acta., 397:60-64 (2008).
Zhang, et al., Genotyping of urinary samples stored with EDTA for forensic applications, Genetics and Molecular Research, 11(3):3007-12 (2012).
Zhou et al., Collection, storage, preservation, and normalization of human urinary exosomes for biomarker discovery, Kidney Int., 69(8):1471-1476 (2006).
Zhou et al., Cyclodextrin functionalized polymers as drug delivery, Polymer Chemistry, 1:1552-1559 (2010).
Zill et al., Cell-free DNA next-generation sequencing in pancreatobiliary carcinomas, Cancer discovery, 5(10):1040-8 (2015).
Luk et al., CTC-mRNA (AR-V7) Analysis from Blood Samples—Impact of Blood Collection Tube and Storage Time, Int. J. Mol. Sci., 18(5):1047 (2017).
Markus et al., Evaluation of pre-analytical factors affecting plasma DNA analysis, Sci. Rep., 8(1):7375 (2017).
Marrinucci et al., Cytomorphology of circulating colorectal tumor cells:a small case series, J. Oncol., 2010:861341 (2010).
Maunier et al., Can stabilization of whole blood samples with Cytochex (Trademark) allow test batching of CD55 and CD59 deficiency flow cytometry analysis?, Cellquant-Redquant CD55/CD59, 1-8 (2012).
McCoy, Ch. 10: Preparation of cells from blood, Methods in Cell Biology, 63 (2001).
Mellert et al., Development and clinical utility of a blood-based test service for the rapid identification of actionable mutations in non-small cell lung carcinoma, J. Mol. Diag., 19(3):404-416 (2017).
Miller-Lindholm et al., Streck cell preservative preserves bone marrow specimens, Streck Cell Preservative Application Note Issue 1, 320024-2, 1-4 (2004).
Minear et al., Global perspectives on clinical adoption of NIPT, Prenat. Diagn., 35(10):959-967 (2015).
Murugesan et al., Investigation of Preanalytical Variables Impacting Pathogen Cell-Free DNA in Blood and Urine, Journal of Clinical Microbiology, 57(11):1-13 (2019).
Nace et al., Evaluation of Streck tissue fixative, a nonformalin fixative for preservation of stool samples and subsequent parasitologic examination, J. Clin. Microbiology, 37(12):4113-4119 (1999).
Nigam et al., Detection of fetal nucleic acid in maternal plasma: A novel noninvasive prenatal diagnostic technique, JIMSA., 25(3):199-200 (2012).
O'Leary et al., The importance of fixation procedures on DNA template and its suitability for solution-phase polymerase chain reaction and PCR in situ hybridization, Histochemical Journal, 26:337-346 (1994).
Parackal et al.. Comparison of Roche Cell-Free DNA collection Tubes (Registered) to Streck Cell-Free DNA BCT (Registered) s for sample stability using healthy volunteers, Pract. Lab. Med., 16:e00125 (2019).
Parpart-Li et al.. The effect of preservative and temperature on the analysis of circulating tumor DNA, Clinical Cancer Research, 23(10):2471-2477 (2017).
Patterson et al., Fixation for in situ molecular analysis. B.K. Patterson (ed.), Techniques in Quantification and Localization of Gene Expression, 23-34 (2000).
Pertl et al., Detection of male and female fetal DNA in maternal plasma by multiplex fluorescent polymerase chain reaction amplification of short tandem repeats, Hum. Genet., 106:45-49 (2000).
Phillips et al., Optical quantification of cellular mass, volume, and density of circulating tumor cells identified in an ovarian cancer patient, Front Oncol., 2:72 (2012).
Phillips et al., Quantification of cellular volume and sub-cellular density fluctuations: comparison of normal peripheral blood cells and circulating tumor cells identified in a breast cancer patient, Front. Oncol, 2:96 (2012).
Pietrzak-Johnston et al., Evaluation of commercially available preservatives for laboratory detection of helminths and protozoa in human fecal specimens, J. Clin. Microbiology, 38(5):1959-1964 (2000).
Qin et al., Stabilization of cfDNA in Urine Using a Preservative Reagent During Sample Processing, Transport, and Storage, Biofluid Biopsies & High-Value Diagnostics Nov. 16-17 and Molecular Medicine Tri-Conference February, held in Boston (2015).
Raptis et al., Quantitation and characterization of plasma DNA in normals and patients with systemic lupus erythematosus, J. Clin. Invest., 66:1391-1399 (1980).
Rintu et al., MRCH, Does formaldehyde increase cell free DNA in maternal plasma specimens?, Laboratory Med., 47(4):286-292 (2016).
Risberg et al., Effects of collection and processing procedures on plasma circulating cell-free DNA from cancer patients, J. Mol. Diagn., 20(6):883-892 (2018).
RNAlater product information, Sigma-aldrich technical bulletin (2016).
Rodriguez-Lee et al., Effect of blood collection tube type and time to processing on the enumeration and high-content characterization of circulating tumor cells using the high-definition single-cell assay, Arch. Pathol. Lab. Med., 142(2):198-207 (2017).
Sacher et al., Prospective validation of rapid plasma genotyping for the detection of EGFR and KRAS mutations in advanced lung cancer, JAMA Oncol., 2(8):1014-22 (2016).
Saxton et al., Effect of ex vivo storage on human peripheral blood neutrophil expression of CD11b and the stabilizing effects of Cyto-Chex, J. Immunol. Methods, 214:11-17 (1998).
Scher et al., Association of AR-V7 on circulating tumor cells as a treatment-specific biomarker with outcomes and survival in castration-resistant prostate cancer, JAMA. Oncol, 2(11):1441-1449 (2016).
Sherwood et al., Optimised pre-analytical methods improve KRAS mutation detection in circulating tumour DNA (ctDNA) from patients with non-small cell lung cancer (NSCLC), PLoS One, 11(2):e0150197 (2016).
Smith et al., Targeted mutation detection in breast cancer using MammaSeq (Trademark), Breast Cancer Research, 21(1):22 (2019).
Springer et al., Evaluation of a new reagent for preserving fresh blood samples and its potential usefulness for internal quality controls of multichannel hematology analyzers, Am. J. Clin. Pathol., 111:387-396 (1999).
Taylor-Phillips et al., Accuracy of non-invasive prenatal testing using cell-free DNA for detection of down, Edwards and patau syndromes: a systematic review and meta-analysis, BMJ. Open., 6(1):e010002 (2016).

(56) References Cited

OTHER PUBLICATIONS

Thompson et al., Detection of therapeutically targetable driver and resistance mutations in lung cancer patients by next-generation sequencing of cell-free circulating tumor DNA, Clin. Cancer Res , 22(23):5772-5782 (2016).
Trigg et al., Factors that influence quality and yield of circulating-free DNA: a systematic review of the methodology Titerature, Heliyon, 4(7):e00699 (2018).
Truett et al., Efficacy of cyto-chex blood preservative for delayed manual CD4 testing using dynal T4 quant CD4 test among HIV-infected persons in Zambia, J. Acquir Immune Defic Syndr., 41(2):168-174 (2006).
Tsui et al., Stability of endogenous and added RNA in blood specimens, serum, and plasma, Clin. Chem., 48:1647-1653(2002).
Turpen et al., A reagent for stabilizing blood samples, American Clinical Laboratory, 15(8):30-31 (1996).
Utting et al., Detection of tumor genetic alterations of bladder carcinomas in body fluids depends on sample treatment before DNA isolation, Annals New York Academy of Sciences, 906:67-71 (2000).
Veldore et al., Validation of liquid biopsy: plasma cell-free DNA testing in clinical management of advanced non-small cell lung cancer, Lung Cancer: Targets and Therapy, 9:1-11 (2018).
Warrino et al., Absolute count data from streck cell preservative treated cells, Streck Cell Preservative Application Note Issue 2, 320520-1, 1-2 (Date Unknown).
Warrino et al., Blood specimens stable in cyto-chex(Registered) BCT at elevated temperatures, Application Note, Issue 3, 20547-2, 1-4 (2006).
Warrino et al., Cyto-chex BCT stabilizes light scatter and cell morphology, Application Note, Issue 2, 320523-1, 1-4 (2005).
Warrino et al., Cyto-chex BCT stabilizes whole blood for seven days for immunophenotyping by flow cytometry, Application Note, Issue 1, 320517-4, 1-2 (2004).
Warrino et al., Cyto-chex(Registered) BCT allows for accurate T-cell counts by flow cytometry 14 days post sample collection, Application Note, Issue 4, 320563-1, 1-2 (Date Unkown).
Warrino et al., Cyto-Chex(Registered) blood collection tube stabilizes samples stored at elevated temperatures for flow cytometry analysis, Streck, Omaha, NE 68128, 1 (Date Unknown).
Warrino et al., Stabilization of white blood cells and immunologic markers for extended analysis using flow cytometry, J. Immunol. Methods., 305:107-119 (2005).
Warrino, Cyto-chex BCT, not cyto-chex, should be used for preservation of CD4 cell counts, JAIDS., 43(4):503-504 (2006).
Weeks, How one laboratory reduced weekend flow cytometry staffing, Clinical Lab Products, 1-4 (2003).
Wijk et al., Detection of apoptotic fetal cells in plasma of pregnant women, Clin. Chem., 46(5):729-731 (2000).
Wollison et al., Blood collection in cell-stabilizing tubes does not impact germline DNA quality for pediatric patients, PLoS One, 12(12):e0188835 (2017).
Alidousty et al., Comparison of blood collection tubes from three different manufacturers for the collection of cell-free DNA for liquid biopsy mutation testing, J. Mol. Diagnostics, 19(5):801-804 (2017).
Amicucci et al., Prenatal diagnosis of myotonic dystrophy using fetal DNA obtained from maternal plasma, Clin. Chem., 46(2):301-302 (2000).
Amitani et al., Allantoin ameliorates chemically-induced pancreatic (Beta)-cell damage through activation of the imidazoline I3 receptors, Peer J., 3:e1105 (2015).
Anker et al., Circulating nucleic acids In plasma and serum as a noninvasive investigation for cancer: Time for Targe-scale clinical studies?, Int. J. Cancer, 103:149-152 (2003).
Augustus et al., The art of obtaining a high yield of cell-free DNA from urine, PLoS ONE, 15(4): e0231058:1-22 (2020).
Benachi et al., Impact of formaldehyde on the in vitro proportion of fetal DNA in maternal plasma and serum, Clin. Chem., 51(1):242-244 (2005).
Bloom et al., Cell-free DNA and active rejection in kidney allografts, J. Am. Soc. Nephrol., 28(7):2221-2232 (2017).
Boffa et al., Cellular expression of PD-L1 in the peripheral blood of lung cancer patients is associated with worse survival, Cancer Epidemiol. Biomarkers Prev., 26(7):1139-1145 (2017).
Brown et al., A novel flow cytometry stimulation assay using cyto-ches(Registered) BCT tubes for use in clinical trials, Flow Contract Site Laboratory, 1 (2011).
Campbell et al., Analytical and biological considerations in the measurement of cell-associated CCR5 and CXCR4 mRNA and protein, Clin. Vaccine Immun., 17(7):1148-1154 (2010).
Camunas-Soler et al., Noninvasive prenatal diagnosis of single-gene disorders by use of droplet digital PCR, Clin. Chem., 64(2):336-345 (2017).
Catellier et al., Atherosclerosis risk in communities (ARIC) carotid MRI flow cytometry study of monocyte and platelet markers: intraindividual variability and reliability, Clinical Chemistry, 54(8):1363-1371 (2008).
Chang et al., Review of the clinical applications and technological advances of circulating tumor DNA in cancer monitoring, The Clin. Risk Manag., 13:1363-1374 (2017).
Chu et al., ESR1 mutations in circulating plasma tumor DNA from metastatic breast cancer patients, Clin. Cancer Res., 22(4):993-999 (2016).
Clausen et al., Noninvasive fetal RhD genotyping, Transfusion and Apheresis Science, (2014).
Davis et al., Stability of immunophenotypic markers in fixed peripheral blood for extended analysis using flow cytometry, J. Immunol. Methods, 363:158-165 (2011).
Dessel et al., Application of circulating tumor DNA in prospective clinical oncology trials—standardization of preanalytical conditions, Mol. Oncol., 11(3):295-304 (2017).
Diaz et al., Performance of streck cfDNA blood collection tubes for liquid biopsy testing, PLoS One, 11(11):e0166354 (2016).
Fan et al., Noninvasive diagnosis of fetal aneuploidy by shotgun sequencing DNA from maternal blood, PNAS., 105(42):16266-16271 (2008).
Fiebelkorn et al., Clinical evaluation of an automated nucleic acid isolation system, Clin. Chem., 48(9): 1613-1615 (2002).
Foy et al., Emerging homogeneous technologies for bioanalysis, Clin. Chem., 47(6)990-100 (2001).
Francis et al., Rapid single step method for flow cytometric detection of surface and intracellular antigens using whole blood, Cytometry, 25:58-70 (1996).
Gahlawat et al., Evaluation of storage tubes for combined analysis of circulating nucleic acids in liquid biopsies, Int. J. Mol. Sci., 20(3):704 (2019).
Gogoi et al., Development of an automated and sensitive microfluidic device for capturing and characterizing circulating tumor cells (CTCs) from clinical blood samples, PLoS One, 11(1):e0147400 (2016).
Greene et al., Chromosomal instability estimation based on next generation sequencing and single cell genome wide copy number variation analysis, PLoS One, 11(11):e0165089 (2016).
Greer et al., PCR amplification from paraffin-embedded tissues, Am. J. Clin. Pathol., 95(2):117-124 (1991).
Grskovic et al., Validation of a clinical-grade assay to measure donor-derived cell-free DNA in solid organ transplant recipients, J. Mol. Diagn., 18(6):890-902 (2016).
Herrera et al., Cell-free DNA, inflammation, and the initiation of spontaneous term labor, Am. J. Obstet. Gynecol., 217(5):583.e1-583.e8 (2017).
Holodniy et al., Determination of human immunodeficiency virus RNA in plasma and cellular viral DNA genotypic zidovudine resistance and viral load during zidovudine-didanosine combination therapy, J. Virology, 69(6):3510-3516 (1995).
Hrebien et al., Reproducibility of digital PCR assays for circulating tumor DNA analysis in advanced breast cancer, PLoS One, 11(10):e0165023 (2016).
Hulien et al., Non-invasive prenatal diagnosis: an epigenetic approach to the detection of common fetal chromosome disorders by analysis of maternal blood samples, Circulating Nucleic Acids In Plasma and Serum, 133-142(2011).

(56) References Cited

OTHER PUBLICATIONS

Hyland et al., Non-invasive fetal RHD genotyping for RhD negative women stratified into RHD gene deletion or variant groups: comparative accuracy using two blood collection tube types, Pathology, 49(7):757-764 (2017).
Jundi et al., Streck cell preservative(Trademark) preserves fine needle aspiration samples for immunophenotyping by flow cytometry, Streck, 1-3 (2021).
Jung et al., Changes in concentration of DNA in serum and plasma during storage of blood samples, Clin. Chem., 49 6 Pt 1:1028-1029 (2003).
Khosrotehrani et al., Fetal cell-free DNA circulates in the plasma of pregnant mice: relevance for animal models of fetomatemal trafficking, Human Reproduction, 19(11):2460-2464 (2004).
Kidess-Sigal et al., Enumeration and targeted analysis of KRAS, BRAF and PIK3CA mutations in CTCs captured by a label-free platform: comparison to ctDNA and tissue in metastatic colorectal cancer, Oncotarget, 7(51):85349-85364 (2016).
Kodym et al., Determination of radiation-induced DNA strand breaks in individual cells by non-radioactive labelling of 3' OH ends, Int. J. Radiat. Biol., 68(2):133-139 (1995).
Kotsopoulou et al., Non-invasive prenatal testing (NIPT): limitations on the way to become diagnosis, Diagnosis, 2(3):141-158 (2015).
Krol et al., Detection of circulating tumour cell clusters in human glioblastoma, Br. J. Cancer, 119(4):487-491 (2018).
Leal-Klevezas et al., Antifreeze solution improves DNA recovery by preserving the integrity of pathogen-infected blood and other tissues, Clin. Diagnostic Laboratory Immun., 7(6):945-946 (2000).
Lee et al., Effect of platelet-associated virus on assays of HIV-1 in plasma, Science, 262:1585-1586 (1993).
Lee et al., Quantitation of genomic DNA in plasma and serum samples: higher concentrations of genomic DNA found in serum than in plasma, Transfusion, 41:276-282 (2001).
Lehmann et al., Characterization and chemistry of imidazolidinyl urea and diazolidinyl urea, Contact Dermatitis, 54(1):50-58 (2006).
Lench et al., The clinical implementation of non-invasive prenatal diagnosis for single-gene disorders: challenges and progress made, Prenat. Diagn., 33(6):555-62 (2013).
Lewis et al., Detecting cancer biomarkers in blood: challenges for new molecular diagnostic and point-of-care tests using cell-free nucleic acids, Expert Rev. Mol. Diagn., 15(9):1187-200 (2015).
Lo et al., Commentary: fetal-derived paternally inherited genetic markers in maternal plasma, from molecular testing in laboratory medicine, AACC Press, 264-265 (2002).
Lo, Fetal DNA in maternal plasma/serum: the first 5 years, Pediatr. Res., 53(1):16-17 (2003).
Locke et al., DNA Methylation Cancer Biomarkers: Translation to the Clinic, Frontiers in Genetics, 10(1150):1-22 (2019).
Lui et al., Circulating DNA in plasma and serum: Biology, Preanalytical issues and diagnostic applications, Clin. Chem. Lab. Med., 40(10):962-968 (2002).
Lui et al., Predominant hematopoietic origin of cell-free DNA in plasma and serum after sex-mismatched bone marrow transplantation, Clinical Chemistry, 48(3):421-427 (2002).
World health organization. Diagnostic imaging and laboratory technology, Use of anticoagulants in diagnostic Taboratory investigations, World Health Organization, (2002).
Yee et al., A novel approach for next-generation sequencing of circulating tumor cells, Mol. Genet. Genomic Med., 4(4):395-406 (2016).
Zhang et al., Detection and characterization of circulating tumour cells in multiple myeloma, J. Circ. Biomark., 5:10 (2016).
Zhong et al., Presence of mitochondrial tRNA(Leu(UUR)) A to G 3243 mutation in DNA extracted from serum and plasma of patients with type 2 diabetes mellitus, J. Clin. Pathol., 53:466-469 (2000).
Ziegler et al., Circulating DNA: a new diagnostic gold mine?, Cancer Treat Rev., 28:255-271 (2002).
European Application No. 18867969, European Search Report and Opinion, dated Jun. 30, 2021.

Jensen et al., High-throughput massively parallel sequencing for fetal aneuploidy detection from maternal plasma, PloS One, 8(3):e57381 (2013).
Jeon et al., The feasibility study of non-invasive fetal trisomy 18 and detection with semiconductor sequencing platform, PLoS One, 9(10):e110240 (2014).
Jodal et al., Investigation of the hemolytic effect of the cyclodextrin derivatives, Proceedings of the Fourth International Symposium on Cyclodextrins, 421-425, (1988).
Kadam et al., Quantitative measurement of cell-free plasma DNA and applications for detecting tumor genetic variation and promoter methylation in a clinical setting, The Journal of Molecular Diagnostics, 14(4):346-56 (2012).
Kagan et al., A Sample Preparation and Analysis System for Indentifieation of Circulating Tumor Cells, Journal of Clinical Ligand Assay, 25(1):104-110 (2002).
Kania et al., Urinary proteases degrade albumin: implications for measurement of albuminuria in stored samples, Annals of Clinical Biochemistry, 47:151-157 (2010).
Kashiwasaki et al., Influence of upper and lower thermoneitral room temperatures (20 °C and 25°C) on fasting and post-prandial resting metabolism under different outdoor temperatures, European Journal of Clinical Nutrition, 44:405-413(1990).
Katz et al., Mass-Volume Equivalents of Common Chemical Solids, Available at <http://www.chymist.com/Mass-volume%20equivalents.pdf>. 4 pages (2007).
Kelly et al., Circulating microRNA as a biomarker of human growth hormone administration to patients, 6(3):234-8 (2014).
Kidess et al., Mutation profiling of tumor DNA from plasma and tumor tissue of colorectal cancer patients with a novel, high-sensitivity multiplexed mutation detection platform, Oncotarget, 6(4):2549-2561 (2015).
Kirkizlar et al., Detection of Clonal and Subclonal Copy-Number Variants in Cell-Free DNA from Patients with Breast Cancer Using a Massively Multiplexed PCR Methodology, Translational Oncology, 8(5):407-16 (2015).
Kreuzer et al., Highly Sensitive and specific Fluorescence Reverse Transcription-PCR Assay for the Pseudogene-free Detection of β-actin Transcripts as Quantitative Reference, Clinical Chemistry, 45(2):297-300 (1999).
Kwee et al., Measurement of Circulating Cell-Free DNA in Relation to 18F-Fluorocholine PET/CT Imaging in Chemotherapy-Treated Advanced Prostate Cancer, Clinical and Translational Science, 5(1):65-70 (2012).
Lambert-Messerlian et al., Feasibility of using plasma rather than serum in first and second trimester multiple marker Down's syndrome screening, Journal of medical screening, 19(4):164-70 (2012).
Lanman et al., Analytical and clinical validation of a digital sequencing panel for quantitative, highly accurate evaluation of cell-free circulating tumor DNA, PloS one, 10(10):e0140712 (2015).
Latifa et al., Comparative Study of Seven Commercial Kits for Human DNA Extraction from Urine Samples Suitable for DNA Biomarker-Based Public Health Studies, Journal of Biomolecular Techniques, 25(4):96-110 (2014).
Leclercq, Interactions between cyclodextrins and cellular components: Towards greener medical applications?, Beilstein J. Org. Chem., 12:2644-62 (2016).
Lee et al., Down Syndrome and Cell-Free Fetal DNA in Archived Maternal Serum, Am. J. Obstet Gynecol, 187(5):1217-21 (2002).
Lee et al., Performance of Momguard, a new non-invasive prenatal testing protocol developed in Korea, Obstetrics & Gynecology Science, 58(5):340-5 (2015).
Lee et al., Survival of Donor Leukocyte Subpopulations in Immunocompetent Transfusion Recipients: Frequent Long-Term Microchimerism in Severe Trauma Patients, Blood, 93:3127-3139 (1999).
Lee et al., The importance of standardization on analyzing circulating RNA, Mol. Diagn. Ther., 21(3):259-268 (2017).
Li, et al., Detection of Paternally Inherited Fetal Point Mutations for 13-Thalassemia Using Size-Fractionated Cell-Free DNA in Maternal Plasma, JAMA., 293(7):843-849 (2005).

(56) References Cited

OTHER PUBLICATIONS

Liao et al., Noninvasive prenatal diagnosis of common aneuploidies by semiconductor sequencing, Proceedings of the National Academy of Sciences, 111(20):7415-20 (2014).

Liberti et al., Bioreceptor Fenofluids: Novel Characteristics and their Utility in Medical Applications, Supplied by the British Library, Kluwer Academic Publishers; (1996).

Liu et al., Placental mosaicism for Trisomy 13: a challenge in providing the cell-free fetal DNA testing, Journal of assisted reproduction and genetics, 31(5):589-94 (2014).

Lo et al., Increased Fetal DNA Concentrations in the Plasma of Pregnant Women Carrying Fetuses with Trisomy 21, Clinical Chemistry, 45(10):1747-1751 (1999).

Lo et al., Noninvasive prenatal diagnosis for fetal chromosomal aneuploidies by maternal plasma nucleic acid analysis, Clinical Chemistry, American Association for Clinical Chemistry, 54(3):461-466 (2008).

Lo, Circulating Nucleic Acids in Plasma and Serum: An Overview, Annals of the New York Academy of Sciences, 945:1-291 (2001).

Lo, Fetal DNA in Maternal Plasma: Biology and Diagnostic Applications, Clinical Chemistry, 46(12):1903-1906 (2000).

Lo, Fetal Nucleic Acids in Maternal Plasma, Toward the Development of Noninvasive Prenatal Diagnosis of Fetal Chromosomal Aneuploidies, New York Academy of Sciences, 1137:140-143 (2008).

Lo, Introduction: Plasma DNA and Urinary DNA, pp. 261-263, from BRUNS et al. (eds.), Molecular Testing in Laboratory Medicine: Selections from Clinical Chemistry, 1998-2001, AACC Press (2002).

Lo, Molecular Testing of Urine: Catching DNA on the way out, Clinical Chemistry, 46(8):1039-40 (2000).

Loftsson et al., Cyclodextrins in drug delivery, Expert Opin. Drug Deliv., 2:335-351 (2005).

Loftsson et al., Self-association of cyclodextrins and cyclodextrin complexes, J. Pharm. Sci., 93(5):1091-1099 (2004).

Lu et al., Detection and Characterization of Circulating Tumour Cells from Frozen Peripheral Blood Mononuclear Cells, Journal of Circulating Biomarkers, 35(12):1243-6 (2015).

Lutz et al., Release of spectrin-free vesicles from human erythrocytes during ATP depletion. I. Characterization of spectrin-free vesicles, J. Cell Biol., 73(3):548-60 (1977).

Machaca et al., Characterization of apoptosis-like endonuclease activity in avian thymocytes, Biology of the Cell, 76(1):15-22 (1992).

Madabusi et al., RNA extraction for arrays, Methods in Enzymology, 411:1-14 (2006).

Mahammad et al., Cholesterol depletion using methyl-beta-cyclodextrin, Methods in Membrane Lipids, 91-102 (2015).

Makhro et al., Red cell properties after different modes of blood transportation, Front Physiol., 7:288 (2016).

May et al., How Many Species Are There On Earth?, Science, 241:1441-1449 (1988).

McCullough et al., Non-invasive prenatal chromosomal aneuploidy testing-clinical experience: 100,000 clinical samples, PLoS One, 9(10):e109173 (2014).

Merriam-Webster's Medical Dictionary, p. 606, Springfield, MA: Merriam-Webster Incorporated (1995).

Milde et al., Improved DNA typing of human urine by adding EDTA, Int. J. Legal Med., 112(3):209-210 (1999).

Miller et al., A Simple Salting Out Procedure for Extracting DNA from Human Nucleated Cells, Nucleic Acids Research, 16(3): 1215 (1988).

Modrek et al., Genome-wide Detection of Alternative Splicing in Expressed Sequences of Human Genes, Nucleic Acid Research, 29(13):2850-2859 (2001).

Motoyama et al., Effect of 2,6-di-O-methyl-alpha-cyclodextrin on hemolysis and morphological change in rabbit's red blood cells, Eur. J. Pharm. Sci., 29(2):111-9 (2006).

Motoyama et al., Involvement of lipid rafts of rabbit red blood cells in morphological changes induced by methylated beta-cyclodextrins, Biol. Pharm. Bull., 32(4):700-5 (2009).

Nair et al., An observational study of circulating tumor cells and (18) F-FDG PET uptake in patients with treatment-naive non-small cell lung cancer, PloS One, 8(7):e67733 (2013).

Nicolaides et al., Validation of targeted sequencing of single-nucleotide polymorphisms for non-invasive prenatal detection of aneuploidy of chromosomes 13,18, 21, X, and Y, Prenatal Diagnosis, 33(6):575-9 (2013).

\* cited by examiner

SINGLE SPIN PROCESS FOR BLOOD PLASMA SEPARATION AND PLASMA COMPOSITION INCLUDING PRESERVATIVE

CROSS-REFERENCE TO RELATED APPLICATIONS

This application is a Continuation of U.S. application Ser. No. 15/355,444, filed Nov. 18, 2016, which claims the priority benefit under 35 U.S.C. § 119(e) of U.S. Provisional Patent Application No. 62/258,404, filed Nov. 20, 2015, the disclosures of each of which are incorporated herein by reference in their entirety.

TECHNICAL FIELD

The teachings relates generally to separation of blood plasma in whole blood for analysis of preserved components.

BACKGROUND

The demonstration by Leon et al. in 1977 that cell-free plasma DNA is elevated in cancer patients paved the way for the present day interest in cell-free plasma nucleic acid in disease diagnosis. More recently, Lo et al. *Lancet* 350 (1997) 485-487 have identified the existence of circulating cell-free fetal nucleic acids in maternal plasma. Since this work, a number of studies have demonstrated that cell-free fetal nucleic acids present in maternal plasma can be used in non-invasive prenatal diagnosis.

The difficulty in obtaining the genetic material of a fetus has presented a number of barriers to testing for the many known genetic markers for hereditary disease, and for other fetal characteristics.

Also in recent years there have been substantial developments in the isolation of circulating tumor cells and their attendant nucleic acids.

For the above testing, and for other newer forms of analysis, it has become recognized that the processes can be best achieved by isolating matter contained in a whole blood draw, preferably by way of a direct blood draw. Certain products (e.g., Cell-free DNA BCT®, Cell-free RNA BCT® and Cyto-Chex BCT®) have been developed and commercialized to address the surprising recognition that certain reagents can be included in a blood collection tube (e.g., agents in addition to a conventional anti-coagulant). See, e.g., U.S. Pat. Nos. 8,304,187 and 8,586,306 and U.S. Patent Publication Nos. 2010/0184069, 2014/0054508, 2011/0111410, 2004/0137417, 2010/0317107, 2014/0080112 and 2014/0199681, all incorporated by reference for all purposes. The agents are selected and used in certain predetermined amounts so that the desired target matter for analysis is preserved for analysis. Another benefit that can be achieved is the preservation of integrity of target nucleic acids, so that further analysis is made readily possible.

In connection with at least the isolation and testing of fetal nucleic acids within maternal blood, early researchers also recognized that certain sample handling techniques were critical to a successful analysis. In particular, work by a team that included one of the industry's pioneer leaders, Dennis Lo, determined that a two-stage centrifugation protocol was critical to quantification of DNA in maternal plasma. See Chiu, et al., "Effects of Blood-Processing Protocols on Fetal and Total DNA Quantification in Maternal Plasma", *Clinical Chemistry* (47:9) 1607-1613 (2001). Under that approach, a sample is centrifuged during a first stage for a first substantial period of time (e.g., about 10 minutes) at a first speed. After the first stage, resulting plasma is removed and subjected to a second stage of centrifugation. The second stage is for a second substantial period of time (e.g., about 10 minutes) at a second speed higher than the first speed, such as by about 10 times. Literature supports that the industry ostensibly has come to accept a two stage centrifugation as a standardized approach. See, e.g., Norton et al., "A New Blood Collection Device Minimizes Cellular DNA Release During Sample Storage and Shipping When Compared to a Standard Device", *Journal of Clinical Laboratory Analysis* (27) 305-311 (2013), Chan et al., "Size Distributions of Maternal and Fetal DNA in Maternal Plasma", *Clinical Chemistry* (50:1) 88-92 (2004) and Fan et al., "Analysis of the Size Distributions of Fetal and Maternal Cell-Free DNA by Paired-End Sequencing", *Clinical Chemistry* (56:8) 1279-1286 (2010), (all incorporated by reference herein for all purposes).

Unfortunately, as can be seen, a process that includes two centrifugations and an intermediate separation step can be tedious, time consuming and potentially difficult to automate. To further increase widespread acceptance of the non-invasive analytical techniques described, it is expected that the industry will need to find ways to assure high quality analysis, while also contributing to a reduction in processing steps that can be a potential source of error.

It would therefore be of great benefit to develop sample processing techniques that would optimize and/or the amount of fetal or other nucleic acids (DNA and/or RNA) recoverable from a whole blood sample while also reducing the time and steps necessary for effective isolation. As a result, the isolation and testing of the nucleic acids may be more reliable and may have improved diagnostic capabilities. It would also be a great benefit if the techniques would employ ingredients that are considered free of any significant amounts (e.g., containing only trace amounts at most) of potentially toxic substances, such as formaldehyde, or other aldehydes.

The present teachings address the need for an efficient and consistent method of preserving and testing nucleic acids from within a plasma separated from a whole blood sample. By providing an improved protocol herein, it is now possible to reproducibly recover nucleic acids (e.g., without limitation, fetal cell free DNA and/or RNA, and/or nucleic acids (e.g., DNA) of circulating tumor matter, mRNA, or other nucleic acid), thereby improving the diagnostic reliability of the nucleic acids, and helping to maintain the structural integrity of the nucleic acids. The present teachings helps prevent contamination of plasma cell-free nucleic acids with cellular nucleic acids that are released from damaged cells, while also allowing the elimination of processing steps conventionally performed in the art. The present teachings further help to inhibit nuclease activity to protect the integrity of the cell-free plasma nucleic acid. The present teachings may further allow for more rapid analysis of blood samples stored at room temperature for up to about 14 days without compromising the integrity of the cell-free nucleic acids present in the plasma and without contaminating the sample with cellular nucleic acids originating from lysed cells. The present teachings may also make it possible to rapidly analyze samples, while avoid any freezing of plasma of a blood sample and/or contact of the sample with any formaldehyde.

One advantage of the present teachings is the possibility for essentially simultaneous stabilizing of both the nucleated blood cells and cell-free nucleic acids. This helps to prevent cellular genomic nucleic acids (e.g., maternal cellular genomic nucleic acids) from being released into plasma, and further diluting the fetal nucleic acids (and associated biomarkers) of interest, while also maintaining the structural integrity of the fetal nucleic acids. An additional possible advantage of the present teachings lies in its ability to maintain relative amounts of fetal nucleic acids, to afford sufficient analysis. The teachings of the present teachings also contemplate the possibility to arrest the degradation of the fetal nucleic acids post-blood draw.

SUMMARY

The present teachings relate generally to a screening method for the identification of a characteristic of a target nucleic acid in a whole blood sample. The method includes a step of positioning a composition comprising whole blood and at least one preservative agent within a centrifuge. A step of centrifugating the composition at a speed of least about 1000 g for at least about 5 minutes to isolate a plasma that includes at least one target nucleic acid for further analysis is performed. There is also a step of analyzing the at least one target nucleic acid to identify a characteristic about the at least one target nucleic acid. The centrifugating step may be performed at a speed that does not exceed about 10,000 g, about 7500 g, about 4500 g, or even about 2500 g, for more than about 3 minutes, about 2 minutes or even about 1 minute. The centrifugating step may be performed at a speed of at least about 500 g, or even about 1500 g.

The preservative agent may be selected from the group consisting of: diazolidinyl urea, imidazolidinyl urea, dimethoylol-5,5dimethylhydantoin, dimethylol urea, 2-bromo-2.-nitropropane-1,3-diol, oxazolidines, sodium hydroxymethyl glycinate, 5-hydroxymethoxymethyl-1-1aza-3,7-dioxabicyclo [3.3.0]octane, 5-hydroxymethyl-1-1aza-3,7dioxabicyclo [3.3.0]octane, 5-hydroxypoly[methyleneoxy]methyl-1-1aza-3,7dioxabicyclo[3.3.0]octane, quaternary adamantine and any combination thereof. For example, the preservative agent may be diazolidinyl urea, imidazolidinyl urea, or a combination thereof. The concentration of the preservative agent prior to the centrifugating step may be between about 1% and about 30%. For example, the concentration of the preservative agent prior to the centrifugating step may be between about 4% and about 10%. The concentration of the preservative agent prior to the centrifugating step may be a concentration at which cross-linking of nucleic acids and proteins is observed, as indicated by agarose gel electrophoresis. The concentration of the preservative agent may be less than about 2% of the blood sample. The composition may further include one or more other nonaqueous ingredients selected from the group consisting of glycine, lysine, ethylene diamine, arginine, urea, adinine, guanine, cytosine, thymine, spermidine, ethylenediaminetetraacetic acid (EDTA), aurintricarboxylic acid (ATA), glyceraldehyde, sodium fluoride or combinations thereof. In such instance, the concentration of the preservative agent to the total volume of the one or more other nonaqueous ingredients may range from about 10:1 to about 1:10. The total time of all centrifugation may be below about 18 minutes, about 16 minutes, or even about 12 minutes.

Other features of the teachings include that the method may be free of any centrifugating at two speeds that differ by a factor of at least about 5:1 (e.g., 7:1 or about 10:1). The method may be such that (i) either or both of the centrifugating or analyzing steps occurs within 14 days after the blood sample is drawn, (ii) either or both of the centrifugating or analyzing steps occurs without freezing the blood sample (e.g. to a temperature colder than about −30° C. (more preferably colder than about −70° C.)); or both (i) and (ii). The method may include a step of providing the composition in a blood collection tube into which the whole blood was directly drawn from a subject and within which the preservative agent was present at the time of the blood draw. The method may be free of any second centrifugating step.

Also within the teachings is a composition including the plasma, the preservative agent, and any other ingredient, which is produced by the method of the present teachings.

As the teachings will illustrate, there is contemplated herein a non-invasive screening method for the identification of characteristics of one or more nucleic acid (e.g., without limitation, fetal cell free DNA and/or RNA, and/or nucleic acids (e.g., DNA) of circulating tumor matter, mRNA, or other nucleic acid) derivable form a whole blood sample, and particularly from separated plasma of a whole blood sample. The method may be regarded generally as having a primarily single centrifugation test protocol for obtaining a plasma containing a ready-for-testing amount of at least one target nucleic acid. The method may be regarded generally as having a centrifugation test protocol for obtaining a plasma containing a ready-for-testing amount of at least one target nucleic acid that can be completed in an amount of centrifugation time of less than about 20 minutes. The method may be regarded generally as having a centrifugation test protocol for obtaining a plasma containing a ready-for-testing amount of at least one target nucleic acid that can be completed in an amount of time less than about 15 minutes. The method may be regarded generally as a having a centrifugation test protocol for obtaining a plasma containing a ready-for-testing amount of at least one target nucleic acid that can be completed in the absence of any centrifugation at a speed in excess of about 2500 g. The method may be regarded generally as having a centrifugation test protocol for obtaining a plasma containing a ready-for-testing amount of at least one target nucleic acid that can be completed so that there is a substantially complete absence (e.g., less than about 0.5 percent by weight of the resulting separated plasma) of any contamination from cellular or other components of the whole blood sample.

DETAILED DESCRIPTION

Figure 1:
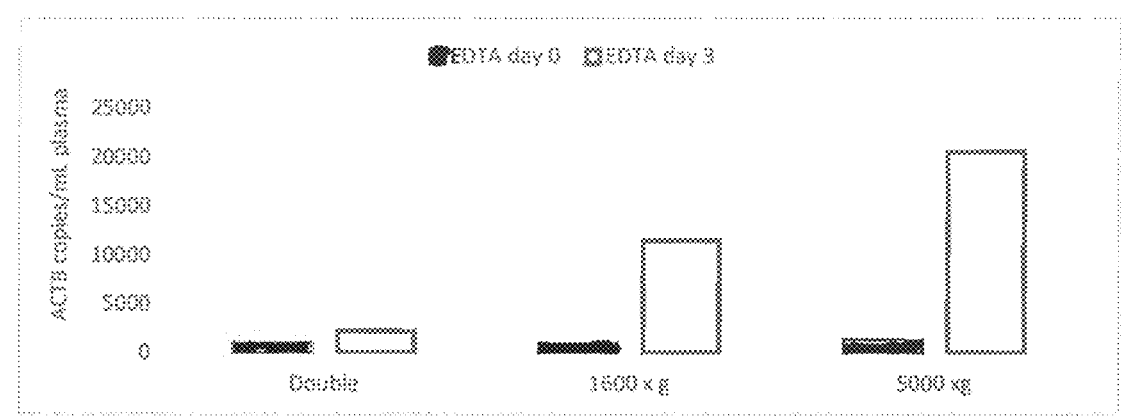
FIG. 1 is an illustrative chart depicting the results of blood plasma cf DNA isolation of post-draw blood samples using EDTA blood collection tubes with a double spin protocol and single spin protocols.

The explanations and illustrations presented herein are intended to acquaint others skilled in the art with the teachings, its principles, and its practical application. Those skilled in the art may adapt and apply the teachings in its numerous forms, as may be best suited to the requirements of a particular use. Accordingly, the specific embodiments of the present teachings as set forth are not intended as being exhaustive or limiting of the teachings. The scope of the teachings should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. Other combinations are also possible as will be gleaned from the following claims, which are also hereby incorporated by reference into this written description.

This application claims the benefit of the filing date of U.S. Provisional Application No. 62/258,404, filed Nov. 20, 2015, the entirety of the contents of that application being hereby incorporated by reference for all purposes.

In general, the teachings herein contemplate a screening method for the identification of a characteristic of a target nucleic acid in a whole blood sample, including positioning a composition comprising whole blood and at least one preservative agent within a centrifuge, centrifugating the composition to isolate a plasma that includes at least one target nucleic acid for further analysis and analyzing the at least one target nucleic acid to identify a characteristic about the at least one target nucleic acid. The method may be free of any second centrifugating step. The nucleic acid may be DNA or RNA or any combination thereof. The teachings also contemplate a composition including the plasma, the preservative agent, and any other ingredient, which is produced by the method.

The method includes contacting a blood sample with a preservative agent. The preservative agent may be selected from the group consisting of diazolidinyl urea, imidazolidinyl urea, dimethoylol-5,5dimethylhydantoin, dimethylol urea, 2-bromo-2.-nitropropane-1,3-diol, oxazolidines, sodium hydroxymethyl glycinate, 5-hydroxymethoxymethyl-1-1aza-3,7-dioxabicyclo[3.3.0]octane, 5-hydroxymethyl-1-1aza-3, 7dioxabicyclo[3.3.0]octane, 5-hydroxypoly[methyleneoxy]methyl-1-1aza-3,7dioxabicyclo [3.3.0] octane, quaternary adamantine, 2-aminoacetic acid or any combination thereof. Preferred ingredients are selected from the group consisting of diazolidinyl urea (DU), imidazolidinyl urea (IDU), and any combination thereof. The preservative agent may be part of a protective agent composition.

The protective agent may consist essentially of the active ingredient. It may be at least about 10%, 50%, or even 80% by volume of the protective agent. For instance, the concentration of active ingredient within the protective agent used may be generally about 10% to about 80%. The concentration of active ingredient within the protective agent may be at least about 25% or even 50%. For example, the protective agent may comprise about 0.05 to about 0.4 grams of a formaldehyde releaser preservation agent (e.g., IDU, DU, or combinations thereof) per 0.2 ml of the total protective agent.

As used throughout the present teachings, the protective agent composition preferably is substantially non-toxic. For example, the methods herein (and compositions used herein) may be free of separately adding and/or handling of any materially significant concentration (e.g., less than about 1% by weight, more preferably less than about 2000 parts per million, more preferably less than about 1000 parts per million, and still more preferably less than about 500 parts per million) of formaldehyde and/or paraformaldehyde prior to any contact with a blood product sample.

The protective agent may include a nuclease inhibitor in a suitable amount to prevent DNase and RNase activity from further decreasing (e.g. by at least about 10% by weight, and more preferably at least about 50% by weight) the quality and amount of nucleic acids recoverable from the blood sample as compared with a sample that does not include a nuclease inhibitor. Nuclease inhibitors that may be used include, but are not limited to diethyl pyrocarbonate, ethanol, aurintricarboxylic acid (ATA), formamide, vanadyl-ribonucleoside complexes, macaloid, ethylenediamine tetraacetic acid (EDTA), proteinase K, heparin, hydroxylamine-oxygen-cupric ion, bentonite, ammonium sulfate, dithiothreitol (DTT), beta-mercaptoethanol, cysteine, dithioerythritol, tris (2-carboxyethyl) phosphene hydrochloride, or a divalent cation such as $Mg^{+2}$, $Mn^{+2}$, $Zn^{+2}$, $Fe^{+2}$, $Ca^{+2}$, $Cu^{+2}$ or any combination thereof. Further, the protective agent may be substantially free of guanidinium salts, sodium dodecyl sulfate (SDS), or any combination thereof.

The protective agent may comprise an active agent in solution. Suitable solvents include water, saline, dimethylsulfoxide, alcohol and mixtures thereof. The protective agent may comprise diazolidinyl urea (DU) and/or imidazolidinyl urea (IDU) in a buffered salt solution. The protective agent may further comprise EDTA and 2-aminoacetic acid. Alternatively, the protective agent may contain only a fixative (e.g., an active ingredient) and may be free of any additional additives.

The amount of any active ingredient within the protective agent may generally be about 10% to about 90% by weight. The active ingredient or fixative may comprise about 70% to about 90% by weight of the protective agent. The protective agent may further contain an anticoagulant such as about 5% to about 20% by weight EDTA. The protective agent may contain about 10% by weight EDTA. The protective agent may include from about 1% to about 40% by weight of nuclease inhibitor.

The amount of active ingredient or fixative (e.g. the formaldehyde releaser) relative to the amount of EDTA may be about 1 to about 10 parts (more preferably about 2 to about 8 parts) by weight of fixative to about 1 part by weight EDTA. The amount of protective agent within a tube prior to blood draw may be about 0.05 to about 1.0 ml and more preferably about 0.1 to about 0.3 ml.

The combination of an active ingredient or fixative (e.g. the formaldehyde releaser) and anticoagulant within the protective agent results in improved ability to maintain the amount and quality of a target nucleic acid within a blood sample. These results are believed unexpected and superior to results obtained by the use of only the fixative or only the anticoagulant. Therefore it is believed that a synergistic effect may occur when both a fixative and anticoagulant are combined. The compositions disclosed herein specifically envision the possibility to include the combination of a formaldehyde releaser and an anticoagulant.

The protective agent may be located within a specialized device, wherein the protective agent is already present in the device prior to addition of the blood sample, such as that disclosed in U.S. Patent Publication No. 2004/0137417, incorporated by reference herein. The device may be an evacuated collection container, usually a tube.

The tube as described above may preferably include an anticoagulant agent and an active ingredient such as a fixative agent including but not limited to those active ingredients disclosed herein. The tube may also may further include a nuclease inhibitor. Preferably, the compounds included in the tube are in an amount sufficient to preserve cell morphology and prevent cell degradation while also preventing deleterious DNase and RNase activity within the cell-free nucleic acids. However, the amount of protective agent may also be sufficiently small so that any consequential dilution of the sample is substantially avoided, and cell-free nucleic acids in the sample are not materially diluted. A blood sample may be fixed simultaneously as it is drawn into the specialized tube.

As discussed herein, contacting a blood or plasma sample with the protective agent allows the sample to be stored for a period of time prior to isolating and testing the nucleic acids. More preferably, a blood or plasma sample may be drawn at one location (e.g., a health care facility), contacted with the protective agent, and later transported to a different remote location (e.g., a laboratory, such as one that is separately housed at a distance of at least about 1 km, 2 km, 3 km, or further away from the draw site) for the nucleic acid isolation and testing process. For example, fetal nucleic acids may be isolated from the maternal blood or plasma sample and tested for various fetal characteristics (including but not limited to chromosomal abnormalities) at the remote location and the resulting diagnostic information may then be reported to the site of the original blood draw.

At any time after the initial contact of the blood or plasma sample with the protective agent, the sample can be treated to isolate the nucleic acids located within the blood sample. The nucleic acids may be isolated using any isolation method including those methods disclosed in U.S. Patent Publication No. 2009/0081678, incorporated by reference herein.

The methods herein thus further contemplate a step of nucleic acid testing. Testing of the nucleic acids can be performed using any nucleic acid testing method including, but not limited to polymerase chain reaction (PCR), reverse transcription polymerase chain reaction (RT-PCR), quantitative real time polymerase chain reaction (Q-PCR), gel electrophoresis, capillary electrophoresis, mass spectrometry, fluorescence detection, ultraviolet spectrometry, DNA hybridization, allele specific polymerase chain reaction, polymerase cycling assembly (PCA), asymmetric polymerase chain reaction, linear after the exponential polymerase chain reaction (LATE-PCR), helicase-dependent amplification (HDA), hot-start polymerase chain reaction, intersequence-specific polymerase chain reaction (ISSR), inverse polymerase chain reaction, ligation mediated polymerase chain reaction, methylation specific polymerase chain reaction (MSP), multiplex polymerase chain reaction, nested polymerase chain reaction, solid phase polymerase chain reaction, or any combination thereof.

One aspect of the teachings herein contemplates a method for isolating and testing cell-free fetal DNA from maternal plasma. The method may be performed on a single sample or on a multitude of samples (e.g., in a multi-well plate). The method may include contacting the maternal plasma sample with a protective agent. The protective agent may include a fixative as previously discussed so that the maternal cells remain intact throughout the blood draw and DNA isolation process. The protective agent may further include a DNase inhibitor to maintain the structural integrity of the fetal DNA. After contacting the maternal plasma sample with the protective agent, the sample may be centrifuged to separate the plasma and the supernatant is discarded. By contacting a maternal blood sample with the protective agent, the blood sample does not necessarily require secondary centrifugation or immediate processing and may be stored for a prolonged period, such as up to about 14 days or longer at room temperature. Thus the teachings herein contemplate one or more steps of storing and/or otherwise waiting a relatively lengthy period from the time of blood draw and/or contacting until the time of screening, testing or other analysis.

Once, the sample is processed, an appropriate concentration of an agent for inducing precipitation (e.g., a composition of salt and/or alcohol) may be added to precipitate the fetal DNA containing material. An organic or other compound such as a phenol derivative or the like may be added to remove any remaining protein contaminants. Any protein contaminants that still remain may be removed by adding additional amounts of an organic or other compound such as a phenol derivative or the like. After centrifugation, ethanol may be added and the sample centrifuged again. Any remaining liquid may be removed from the sample so only the fetal DNA will remain. The finished product of isolated fetal DNA may then be contacted with a buffer.

One or more steps of incubation may be performed. Incubation may occur on ice or at any temperature between −30° C. and 70° C. For example, a sample may be incubated at about −20° C. A sample may also be stored at room temperature and thus substantially free of freezing upon blood draw. The sample may be substantially free of freezing at any time between blood draw and any downstream processing (e.g., isolation and/or analysis).

Centrifugation may be performed at a suitable rate. For example, centrifugation may be done at about 500 to about 20,000 rpm. Centrifugation may occur at about 1,000 to 16,000 rpm. Centrifugation may be performed at about room temperature or cooler. For example, it may be performed at about 1-20° C., or still more specifically at about 4-9° C.

The protective agent of the present teachings may be placed within a tube so that the tube contains about 0.20 ml of the protective agent. The tube containing the protective agent may receive about 10 ml of patient blood. The patient blood may be drawn directly into the tube containing the protective agent.

The protective agent may include a preserving agent and an anticoagulant. The preserving agent may be imidazolidinyl urea or diazolidinyl urea. The imidazolidinyl urea may be present in an amount of about 300 g/l to about 700 g/l of the protective agent. The imidazolidinyl urea may be about 0.05% to about 3% of the protective agent. The diazolidinyl urea may be present in an amount of about 50 g/l to about 400 g/l of the protective agent. The diazolidinyl urea may be about 0.05% to about 2.5% of the protective agent. The anticoagulant may be selected from the group consisting of ethylenediaminetetraacetic acid (EDTA), salts of EDTA, heparin, citrate, oxalate, and any combination thereof. The anticoagulant may be K3EDTA. The K3EDTA may be present in an amount of about 20 g/l to about 150 g/l of the protective agent. The K3EDTA may be present in an amount of about 50 g/l to about 100 g/l of the protective agent. The protective agent may include a preserving agent, an anticoagulant and glycine. The glycine may be present in an amount of about 10 g/l to about 150 g/l of the protective agent. The glycine may be present in an amount of about 35 g/l to about 100 g/l of the protective agent. The protective agent may include a preserving agent, an anticoagulant and ingredients selected from the group consisting of glyceraldehyde, sodium fluoride (NaF), aurintricarboxylic acid (ATA), or combinations thereof. The glyceraldehyde may be present in amount of about 10 g/l to about 150 g/l of the protective agent. The glyceraldehyde may be present in amount of about 35 g/l to about 100 g/l of the protective agent. The sodium fluoride (NaF) may be present in an amount of about 0.1 g/l to about 30 g/l of the protective agent. The sodium fluoride (NaF) may be present in an amount of about 0.05 g/l to about 10 g/l of the protective agent. The aurintricarboxylic acid (ATA) may be present in an amount of about 1 g/l to about 40 g/l of the protective agent. The aurintricarboxylic acid (ATA) may be present in an amount of about 5 g/l to about 20 g/l of the protective agent.

Double spin protocols are commonly used to separate blood plasma for cfDNA isolation. Double spin protocols start with a low speed spin to minimize cell lysis during the plasma isolation step, potentially caused by centrifugation spin speed, followed by high speed centrifugation to remove the low quantity of residual cells remaining. The two spin process is a lengthy/time consuming step in the specimen processing procedure. Table 1 depicts a comparison of two different double spin protocols and a single spin protocol.

TABLE 1

| Double Spin Protocol A | Double Spin Protocol B | Single Spin Protocol |
| --- | --- | --- |
| 300 g for 20 minutes | 1600 g for 15 minutes | 1600 g for 15 minutes |
| Transfer plasma to a new tube (20 samples) 15 minutes | Transfer plasma to a new tube (20 samples) 15 minutes | Collect cell-free plasma for DNA isolation |
| 5,000 g for 10 minutes | 16,000 g for 10 minutes | |
| Collect cell-free plasma for DNA isolation | Collect cell-free plasma for DNA isolation | |
| Estimated Total Time: 45 minutes | Estimated Total Time: 40 minutes | Estimated Total Time: 15 minutes |

In verifying the protective capabilities of the compositions disclosed herein, standard EDTA blood collection tubes are thus compared against cell free nucleic acid blood collection tubes containing the protective agent of the present teachings, which thus contains a composition that stabilizes nucleated blood cells and inhibits plasma nucleases. The results of a double spin protocol and single spin protocols for blood plasma cfDNA isolation of blood samples collected in the respective tubes are also compared.

EXAMPLE 1

Blood was collected into EDTA blood collection tubes and divided into 3 groups for a double spin process of 300×g for 20 min followed by 5000×g for 10 min, a single spin process of 1600×g for 15 minutes, and a single spin process of 5000×g for 15 minutes, respectively. Samples were stored at room temperature and cf DNA was isolated on day 0 and day 3. Total plasma cfDNA was assayed by droplet digital PCR. The comparison of the cell-free DNA concentrations in plasma revealed a statistically significant difference between the samples. FIG. 1 illustrates the results of blood plasma cfDNA isolation of post-draw blood samples using EDTA blood collection tubes and double spin protocols and a single spin protocol. The findings indicate that the double spin protocol is preferred over a single spin protocol with blood collected in EDTA blood collection tubes for isolation of plasma cfDNA.

EXAMPLE 2

Figure 2:
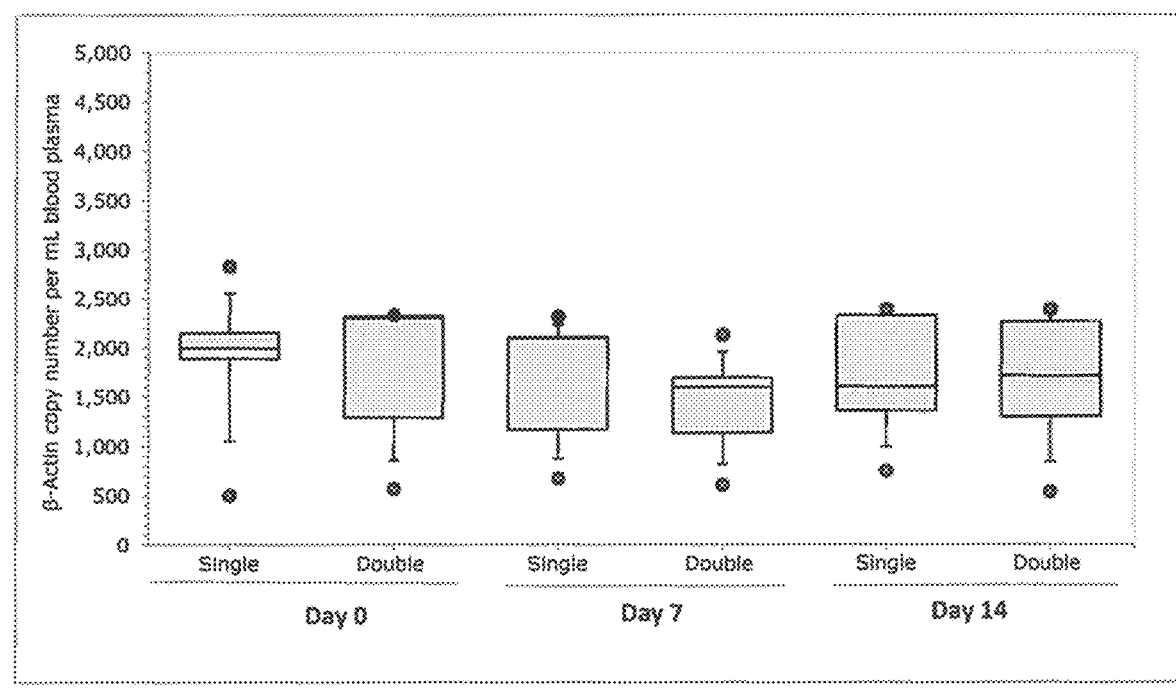
FIG. 2 is an illustrative chart depicting the results of blood plasma cf DNA isolation of post-draw blood samples stored at room temperature using cell-free nucleic acid blood collection tubes with a double spin protocol and a single spin protocol.

Blood was collected into 10 mL cell-free nucleic acid blood collection tubes of the present teachings and divided into 2 groups for the single spin process (i.e. 1600×g for 15 min) and the double spin process (i.e. 300×g for 20 min followed by 5000×g for 10 min), respectively. Samples were stored at room temperature and cfDNA was isolated on day 0, 7, and 14. Total plasma cf DNA was assayed by droplet digital PCR. The comparison of the cell-free DNA concentrations in plasma revealed no statistically significant difference between "paired samples" (i.e. single spin vs. double spin) in the storage study. FIG. 2 illustrates the results of blood plasma cfDNA isolation of post-draw blood samples stored at room temperature using cell-free nucleic acid blood collection tubes and a double spin protocol and a single spin protocol. The findings indicate that the single spin protocol is compatible with the plasma separation procedure from blood collected in cell-free nucleic acid blood collection tubes for isolation of plasma cfDNA. The results for samples tested one or two weeks after the blood draw are not expected to vary by more than +/−10%.

EXAMPLE 3

Figure 3:
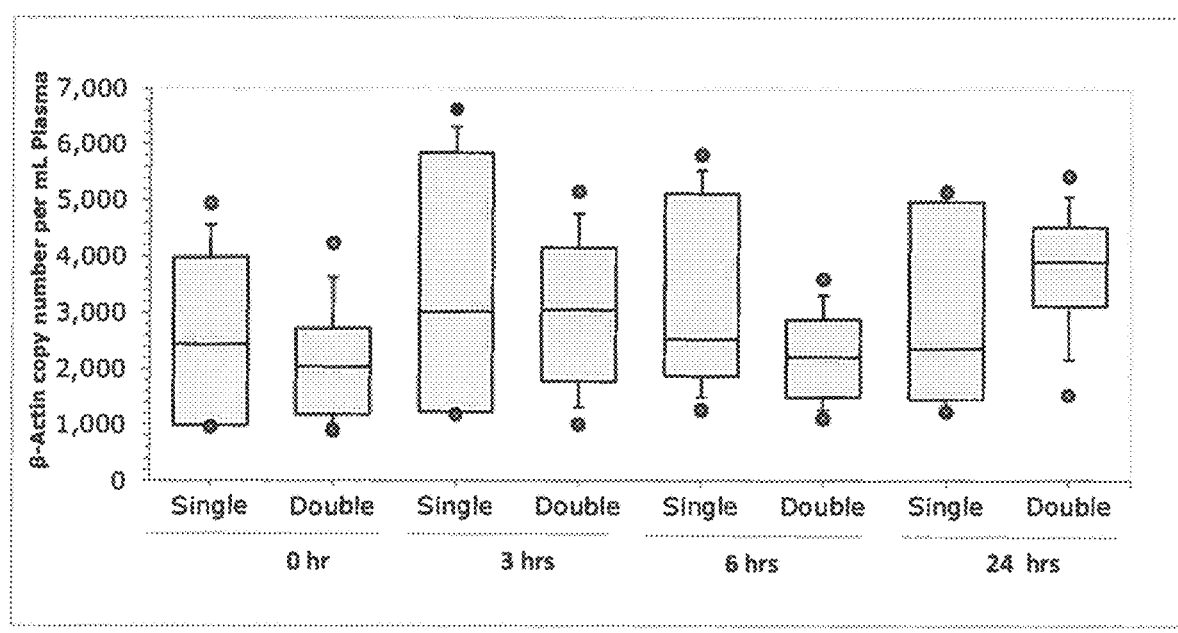
FIG. 3 is an illustrative chart depicting the results of blood plasma cf DNA isolation of post-draw blood samples shaken for selected time intervals using cell-free nucleic acid blood collection tubes with a double spin protocol and a single spin protocol.

Blood was collected into 10 mL cell-free nucleic acid collection tubes of the present teachings and divided into 2 groups for the single spin process (i.e. 1600×g for 15 min) and the double spin process (i.e. 300×g for 20 min followed by 5000×g for 10 min), respectively. The single spin protocol was compared with the double spin protocol in a shaking study to simulate conditions that may occur during sample shipping. Samples were shaken for time intervals of 0 hours, 3 hours, 6 hours and 24 hours. Total plasma cf DNA was assayed by droplet digital PCR. The comparison of the cell-free DNA concentrations in plasma revealed no statistically significant difference between "paired samples" (i.e. single spin vs. double spin) at each shaking time point (n=5 donors). FIG. 3 illustrates the results of blood plasma cf DNA isolation of post-draw blood samples shaken for selected time intervals using cell-free nucleic acid blood collection tubes and a double spin protocol and a single spin protocol. The findings indicate that the single spin protocol is compatible with the plasma separation procedure from blood collected in cell-free nucleic acid blood collection tubes for isolation of plasma cfDNA.

The examples and testing results discussed above demonstrate the merits of a "single spin protocol" for plasma DNA isolation from blood stored in cell-free nucleic acid blood collection tubes of the present teachings without introducing cellular DNA contamination. The double spin protocol was developed for blood drawn into regular tubes, e.g. EDTA tubes. The findings indicate that a double spin protocol is preferred over a single spin protocol with blood collected in EDTA blood collection tubes. However, a single spin protocol is compatible for use with blood samples collected and "stabilized" into cell-free nucleic blood collection tubes of the present teachings. The single spin protocol allows for plasma DNA isolation from blood stored in cell-free nucleic blood collection tubes without introducing cellular DNA contamination.

It will be appreciated that concentrates or dilutions of the amounts recited herein may be employed. In general, the relative proportions of the ingredients recited will remain the same. Thus, by way of example, if the teachings call for 30 parts by weight of a Component A, and 10 parts by weight of a Component B, the skilled artisan will recognize that such teachings also constitute a teaching of the use of Component A and Component B in a relative ratio of 3:1. Teachings of concentrations in the examples may be varied within about 25% (or higher) of the stated values and similar results are expected.

It will be appreciated that the above is by way of illustration only. Other ingredients may be employed in any of the compositions disclosed herein, as desired, to achieve the desired resulting characteristics. Examples of other ingredients that may be employed include antibiotics, anesthetics, antihistamines, preservatives, surfactants, antioxidants, unconjugated bile acids, mold inhibitors, nucleic acids, pH adjusters, osmolarity adjusters, polymers (e.g., PVP, PEG, cyclodextrin) or any combination thereof.

It should be recognized that in the present teachings, unless otherwise stated, reference in a teaching to the generic form of "nucleic acid" contemplates not only the genus of nucleic acids, but also individual species of nucleic acid (such as fetal DNA, fetal RNA, DNA, RNA, mRNA, tumor DNA, tumor RNA, or otherwise) even if such species is not referenced in the passage at hand.

As used herein, unless otherwise stated, the teachings envision that any member of a genus (list) may be excluded from the genus; and/or any member of a Markush grouping may be excluded from the grouping.

Unless otherwise stated, any numerical values recited herein include all values from the lower value to the upper value in increments of one unit provided that there is a separation of at least 2 units between any lower value and any higher value. As an example, if it is stated that the amount of a component, a property, or a value of a process variable such as, for example, temperature, pressure, time and the like is, for example, from 1 to 90, preferably from 20 to 80, more preferably from 30 to 70, it is intended that intermediate range values such as (for example, 15 to 85, 22 to 68, 43 to 51, 30 to 32 etc.) are within the teachings of this specification. Likewise, individual intermediate values are also within the present teachings. For values which are less than one, one unit is considered to be 0.0001, 0.001, 0.01 or 0.1 as appropriate. These are only examples of what is specifically intended and all possible combinations of numerical values between the lowest value and the highest value enumerated are to be considered to be expressly stated in this application in a similar manner. As can be seen, the teaching of amounts expressed as "parts by weight" herein also contemplates the same ranges expressed in terms of percent by weight. Thus, an expression in the Detailed Description of the Teachings of a range in terms of at "'x' parts by weight of the resulting composition" also contemplates a teaching of ranges of same recited amount of "x" in percent by weight of the resulting composition."

Unless otherwise stated, all ranges include both endpoints and all numbers between the endpoints. The use of "about" or "approximately" in connection with a range applies to both ends of the range. Thus, "about 20 to 30" is intended to cover "about 20 to about 30", inclusive of at least the specified endpoints. The disclosures of all articles and references, including patent applications and publications, are incorporated by reference for all purposes. The term "consisting essentially of to describe a combination shall include the elements, ingredients, components or steps identified, and such other elements ingredients, components or steps that do not materially affect the basic and novel characteristics of the combination. The use of the terms "comprising" or "including" to describe combinations of elements, ingredients, components or steps herein also contemplates embodiments that consist essentially of (namely, the presence of any additional elements, ingredients, components or steps, does not materially affect the properties and/or benefits derived from the teachings; for example, the inclusion of a second very brief centrifugation step, such as for less than about 20%, 15%, 10% of the time of the primary centrifugation step described herein) or even consist of the elements, ingredients, components or steps.

Plural elements, ingredients, components or steps can be provided by a single integrated element, ingredient, component or step. Alternatively, a single integrated element, ingredient, component or step might be divided into separate plural elements, ingredients, components or steps. The disclosure of "a" or "one" to describe an element, ingredient, component or step is not intended to foreclose additional elements, ingredients, components or steps. All references herein to elements or metals belonging to a certain Group refer to the Periodic Table of the Elements published and copyrighted by CRC Press, Inc., 1989. Any reference to the Group or Groups shall be to the Group or Groups as reflected in this Periodic Table of the Elements using the IUPAC system for numbering groups.

It is understood that the above description is intended to be illustrative and not restrictive. Many embodiments as well as many applications besides the examples provided will be apparent to those of skill in the art upon reading the above description. The scope of the teachings should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. The omission in the following claims of any aspect of subject matter that is disclosed herein is not a disclaimer of such subject matter, nor should it be regarded that the inventors did not consider such subject matter to be part of the disclosed inventive subject matter.

The explanations and illustrations presented herein are intended to acquaint others skilled in the art with the teachings, its principles, and its practical application. Those skilled in the art may adapt and apply the teachings in its numerous forms, as may be best suited to the requirements of a particular use. Accordingly, the specific embodiments of the present teachings as set forth are not intended as being exhaustive or limiting of the teachings. The scope of the teachings should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. Other combinations are also possible as will be gleaned from the following claims, which are also hereby incorporated by reference into this written description.

The invention claimed is:

1. A method for identifying a characteristic of a target nucleic acid in a whole blood sample, comprising the steps of:
   a. positioning a composition comprising whole blood and a protective agent comprising at least one preservative agent within a centrifuge, wherein the preservative agent is selected from the group consisting of: diazolidinyl urea, imidazolidinyl urea, dimethoylol-5,5dimethylhydantoin, dimethylol urea, 2-bromo-2.-nitropropane-1,3-diol, oxazolidines, sodium hydroxymethyl glycinate, 5-hydroxymethoxymethyl-1-1aza-3,7-dioxabicyclo [3.3.0]octane, 5-hydroxymethyl- 1-1 aza-3, 7dioxabicyclo[3.3.0]octane, 5-hydroxypoly[methyleneoxy]methyl-1-1 aza-3, 7dioxabicyclo[3.3.0]octane, quaternary adamantine and any combination thereof;

b. centrifugating the composition at a speed of at least about 1000 g and below about 4500 g for at least about 5 minutes and less than about 20 minutes to isolate a plasma that includes the target nucleic acid for further analysis;

c. isolating and testing the target nucleic acid obtained from step b to identify the characteristic of the target nucleic acid, wherein the method is free of any second centrifugating step, and wherein the target nucleic acid is cell-free plasma nucleic acid.

2. The method of claim 1, wherein the concentration of the preservative agent prior to the centrifugating step is between about 1% and about 30%.

3. The method of claim 1, wherein the concentration of the preservative agent is less than about 2% of the blood sample.

4. The method of claim 1, wherein the composition further includes one or more other nonaqueous ingredients selected from the group consisting of glycine, lysine, ethylene diamine, arginine, urea, adenine, guanine, cytosine, thymine, spermidine, ethylenediaminetetraacetic acid (EDTA), aurintricarboxylic acid (ATA), glyceraldehyde, and sodium fluoride.

5. The method of claim 1, wherein the centrifugating step consists of a single step of centrifugating the composition at a speed below about 2500 g.

6. The method of claim 1, wherein the centrifugating step consists of a single step of centrifugating the composition at a speed of at least about 1500 g.

7. The method of claim 1, wherein the total time of the centrifugation is below about 18 minutes.

8. The method of claim 1, wherein one or more of the centrifugating, isolating, or testing steps occurs within 14 days after the blood sample is drawn.

9. The method of claim 1, wherein the characteristic is a chromosomal abnormality.

10. The method of claim 1, wherein the centrifugating is performed at room temperature.

11. The method of claim 1, wherein the testing step includes performing droplet digital PCR.

12. The method of claim 1, wherein the total time of centrifugation is below about 12 minutes.

13. The method of claim 1, wherein one or more of the centrifugating, isolating, or testing steps occurs without freezing the blood sample.

14. The method of claim 1 wherein the testing step includes performing polymerase chain reaction (PCR), reverse transcription polymerase chain reaction (RT-PCR), quantitative real time polymerase chain reaction (Q-PCR), gel electrophoresis, capillary electrophoresis, mass spectrometry, fluorescence detection, ultraviolet spectrometry, DNA hybridization, allele specific polymerase chain reaction, polymerase cycling assembly (PCA), asymmetric polymerase chain reaction, linear after the exponential polymerase chain reaction (LATE-PCR), helicase-dependent amplification (HDA), hot-start polymerase chain reaction, intersequence-specific polymerase chain reaction (ISSR), inverse polymerase chain reaction, ligation mediated polymerase chain reaction, methylation specific polymerase chain reaction (MSP), multiplex polymerase chain reaction, nested polymerase chain reaction, solid phase polymerase chain reaction, or a combination thereof.

15. The method of claim 1, wherein the protective agent comprises about 0.05 to about 0.4 grams of the at least one preservative agent per 0.2 ml of the protective agent.

16. The method of claim 4, wherein the EDTA is K3EDTA.

17. The method of claim 4, wherein the EDTA is present in an amount of about 20 g/l to about 150 g/l of the protective agent.

18. The method of claim 17, wherein the EDTA is present in an amount of about 50 g/l to about 100 g/l of the protective agent.

19. The method of claim 4, wherein the glycine is present in an amount of about 10 g/l to about 150 g/l of the protective agent.

20. The method of claim 19, wherein the glycine is present in an amount of about 35 g/l to about 100 g/l of the protective agent.

21. The method of claim 1, wherein the imidazolidinyl urea is present in an amount of about 300 g/l to about 700 g/l of the protective agent.

22. The method of claim 1, wherein the diazolidinyl urea is present in an amount of about 50 g/l to about 400 g/l of the protective agent.

23. The method of claim 1, wherein the composition comprises about 0.05 to about 1.0 ml of the protective agent.

24. The method of claim 1, wherein the composition comprises about 0.1 to about 0.3 ml of the protective agent.

25. The method of claim 1, wherein the composition comprises about 0.2 ml of the protective agent.

26. The method of claim 1, wherein the composition comprises about 10 ml of the whole blood.

27. A method for identifying a characteristic of a target nucleic acid in a whole blood sample comprising the steps of:

a. positioning a composition comprising whole blood and a protective agent comprising at least one preservative agent within a centrifuge, wherein the preservative agent is selected from the group consisting of: diazolidinyl urea, imidazolidinyl urea, dimethoylol-5,5dimethylhydantoin, dimethylol urea, 2-bromo-2.-nitropropane-1,3-diol, oxazolidines, sodium hydroxymethyl glycinate, 5-hydroxymethoxymethyl-1-1aza-3,7- dioxabicyclo [3.3.0]octane, 5-hydroxymethyl-1-1aza-3,7dioxabicyclo[3.3.0]octane, 5- hydroxypoly[methyleneoxy]methyl-1-1aza-3, 7dioxabicyclo[3.3.0]octane, quaternary adamantine and any combination thereof;

b. centrifugating the composition at a speed of about 1600 g for about 15 minutes to isolate a plasma that includes the target nucleic acid for further analysis; and c. isolating and testing the target nucleic acid obtained from step b to identify the characteristic of the target nucleic acid, wherein the method is free of any second centrifugating step, and wherein the target nucleic acid is cell-free plasma nucleic acid.

28. The method of claim 27, wherein the characteristic is a chromosomal abnormality.

29. The method of claim 27, wherein the concentration of the preservative agent prior to the centrifugating step is between about 1% and about 30%.

30. The method of claim 27, wherein the composition further includes one or more other nonaqueous ingredients selected from the group consisting of glycine, lysine, ethylene diamine, arginine, urea, adenine, guanine, cytosine, thymine, spermidine, ethylenediaminetetraacetic acid (EDTA), aurintricarboxylic acid (ATA), glyceraldehyde, and sodium fluoride.

31. The method of claim 27, wherein the centrifugating is performed at room temperature.

32. The method of claim 27, wherein the testing step includes performing droplet digital PCR.

33. The method of claim 27, wherein the total time of centrifugation is below about 12 minutes.

34. The method of claim 27, wherein the concentration of the preservative agent is less than about 2% of the blood sample.

35. The method of claim 27, wherein one or more of the centrifugating, isolating, or testing steps occurs within 14 days after the blood sample is drawn.

36. The method of claim 27 wherein the testing step includes performing polymerase chain reaction (PCR), reverse transcription polymerase chain reaction (RT-PCR), quantitative real time polymerase chain reaction (Q-PCR), gel electrophoresis, capillary electrophoresis, mass spectrometry, fluorescence detection, ultraviolet spectrometry, DNA hybridization, allele specific polymerase chain reaction, polymerase cycling assembly (PCA), asymmetric polymerase chain reaction, linear after the exponential polymerase chain reaction (LATE-PCR), helicase-dependent amplification (HDA), hot-start polymerase chain reaction, intersequence-specific polymerase chain reaction (ISSR), inverse polymerase chain reaction, ligation mediated polymerase chain reaction, methylation specific polymerase chain reaction (MSP), multiplex polymerase chain reaction, nested polymerase chain reaction, solid phase polymerase chain reaction, or a combination thereof.

37. The method of claim 27, wherein the protective agent comprises about 0.05 to about 0.4 grams of the at least one preservative agent per 0.2 ml of the protective agent.

38. The method of claim 30, wherein the EDTA is $K_3$EDTA.

39. The method of claim 30, wherein the EDTA is present in an amount of about 20 g/l to about 150 g/l of the protective agent.

40. The method of claim 39, wherein the EDTA is present in an amount of about 50 g/l to about 100 g/l of the protective agent.

41. The method of claim 30, wherein the glycine is present in an amount of about 10 g/l to about 150 g/l of the protective agent.

42. The method of claim 41, wherein the glycine is present in an amount of about 35 g/l to about 100 g/l of the protective agent.

43. The method of claim 27, wherein the imidazolidinyl urea is present in an amount of about 300 g/l to about 700 g/l of the protective agent.

44. The method of claim 27, wherein the diazolidinyl urea is present in an amount of about 50 g/l to about 400 g/l of the protective agent.

45. The method of claim 27, wherein the composition comprises about 0.05 to about 1.0 ml of the protective agent.

46. The method of claim 27, wherein the composition comprises about 0.1 to about 0.3 ml of the protective agent.

47. The method of claim 27, wherein the composition comprises about 0.2 ml of the protective agent.

48. The method of claim 27, wherein the composition comprises about 10 ml of the whole blood.

* * * * *